US009259569B2

(12) United States Patent
Brounstein et al.

(10) Patent No.: US 9,259,569 B2
(45) Date of Patent: Feb. 16, 2016

(54) METHODS, SYSTEMS AND DEVICES FOR NEUROMODULATING SPINAL ANATOMY

(76) Inventors: Daniel M. Brounstein, San Francisco, CA (US); Albert G. Burdulis, San Francisco, CA (US); Christopher D. Summa, Santa Cruz, CA (US)

( * ) Notice: Subject to any disclaimer, the term of this patent is extended or adjusted under 35 U.S.C. 154(b) by 77 days.

(21) Appl. No.: 12/780,696

(22) Filed: May 14, 2010

(65) Prior Publication Data
US 2010/0292769 A1 Nov. 18, 2010

Related U.S. Application Data

(60) Provisional application No. 61/178,847, filed on May 15, 2009.

(51) Int. Cl.
*A61N 1/05* (2006.01)
*A61N 1/36* (2006.01)

(52) U.S. Cl.
CPC .......... *A61N 1/0551* (2013.01); *A61N 1/36071* (2013.01); *A61N 1/0558* (2013.01)

(58) Field of Classification Search
USPC .................................................. 607/117, 46
See application file for complete search history.

(56) References Cited

U.S. PATENT DOCUMENTS

| 525,891 | A | 9/1894 | Fricke |
| 3,724,467 | A | 4/1973 | Avery et al. |
| 3,845,770 | A | 11/1974 | Theeuwes et al. |
| 3,916,899 | A | 11/1975 | Theeuwes et al. |
| 4,141,367 | A | 2/1979 | Ferreira |
| 4,232,679 | A | 11/1980 | Schulman |
| 4,298,003 | A | 11/1981 | Theeuwes et al. |
| 4,313,448 | A | 2/1982 | Stokes |
| 4,374,527 | A | 2/1983 | Iversen |
| 4,479,491 | A | 10/1984 | Martin |
| 4,549,556 | A | 10/1985 | Tarjan et al. |
| 4,573,481 | A | 3/1986 | Bullara |
| 4,577,642 | A | 3/1986 | Stokes |

(Continued)

FOREIGN PATENT DOCUMENTS

| CN | 2401142 Y | 10/2000 |
| CN | 101594907 A | 12/2009 |

(Continued)

OTHER PUBLICATIONS

The Peripheral Nervous System, http://cnx.org/content/m44751/latest/.*

(Continued)

*Primary Examiner* — Paula J Stice

(57) ABSTRACT

Devices, systems and methods for treating pain or other conditions while minimizing possible complications and side effects. Treatment typically includes electrical stimulation and/or delivery of pharmacological or other agents with the use of a lead or catheter. The devices, systems and methods provide improved anchoring which reduces migration of the lead yet allows for easy repositioning or removal of the lead if desired. The devices, systems and methods also provide for simultaneous treatment of multiple targeted anatomies. This shortens procedure time and allows for less access points, such as needle sticks to the epidural space, which in turn reduces complications, such as cerebral spinal fluid leaks, patient soreness and recovery time. Other possible complications related to the placement of multiple devices are also reduced.

6 Claims, 20 Drawing Sheets

(56) References Cited

U.S. PATENT DOCUMENTS

| | | |
|---|---|---|
| 4,590,946 A | 5/1986 | Loeb |
| 4,607,639 A | 8/1986 | Tanagho et al. |
| 4,739,764 A | 4/1988 | Lue et al. |
| 4,786,155 A | 11/1988 | Fantone et al. |
| 4,803,988 A | 2/1989 | Thomson |
| 4,920,979 A | 5/1990 | Bullara |
| 4,940,065 A | 7/1990 | Tanagho et al. |
| 4,950,270 A | 8/1990 | Bowman et al. |
| 4,976,711 A | 12/1990 | Parins et al. |
| 5,135,525 A | 8/1992 | Biscoping et al. |
| 5,270,099 A | 12/1993 | Kamiyama et al. |
| 5,299,569 A | 4/1994 | Wernicke et al. |
| 5,344,438 A | 9/1994 | Testerman et al. |
| 5,358,514 A | 10/1994 | Schulman et al. |
| 5,370,644 A | 12/1994 | Langberg |
| 5,411,537 A | 5/1995 | Munshi et al. |
| 5,411,540 A | 5/1995 | Edell et al. |
| 5,417,719 A | 5/1995 | Hull et al. |
| 5,419,763 A | 5/1995 | Hilderbrand |
| 5,458,626 A | 10/1995 | Krause |
| 5,489,294 A | 2/1996 | McVenes et al. |
| 5,505,201 A | 4/1996 | Grill et al. |
| 5,514,175 A | 5/1996 | Kim et al. |
| 5,584,835 A | 12/1996 | Greenfield |
| 5,634,462 A | 6/1997 | Tyler et al. |
| 5,643,330 A | 7/1997 | Holsheimer et al. |
| 5,702,429 A | 12/1997 | King |
| 5,711,316 A | 1/1998 | Elsberry et al. |
| 5,713,922 A | 2/1998 | King |
| 5,733,322 A | 3/1998 | Starkebaum |
| 5,741,319 A | 4/1998 | Woloszko et al. |
| 5,755,750 A | 5/1998 | Petruska et al. |
| 5,776,170 A | 7/1998 | MacDonald et al. |
| 5,807,339 A | 9/1998 | Bostrom et al. |
| 5,824,021 A | 10/1998 | Rise |
| 5,865,843 A | 2/1999 | Baudino |
| 5,871,531 A | 2/1999 | Struble |
| 5,885,290 A | 3/1999 | Guerrero et al. |
| 5,938,690 A | 8/1999 | Law et al. |
| 5,948,007 A | 9/1999 | Starkebaum et al. |
| 5,957,965 A | 9/1999 | Moumane et al. |
| 5,983,141 A | 11/1999 | Sluijter et al. |
| 5,984,896 A | 11/1999 | Boyd |
| 6,002,964 A | 12/1999 | Feler et al. |
| 6,044,297 A | 3/2000 | Sheldon et al. |
| 6,045,532 A | 4/2000 | Eggers et al. |
| 6,051,017 A | 4/2000 | Loeb et al. |
| 6,104,957 A * | 8/2000 | Alo et al. ................ 607/46 |
| 6,120,467 A | 9/2000 | Schallhorn |
| 6,161,048 A | 12/2000 | Sluijter et al. |
| 6,175,764 B1 | 1/2001 | Loeb et al. |
| 6,181,965 B1 | 1/2001 | Loeb et al. |
| 6,185,455 B1 | 2/2001 | Loeb et al. |
| 6,205,359 B1 | 3/2001 | Boveja |
| 6,208,902 B1 | 3/2001 | Boveja |
| 6,214,016 B1 | 4/2001 | Williams et al. |
| 6,259,952 B1 | 7/2001 | Sluijter et al. |
| 6,298,256 B1 | 10/2001 | Meyer |
| 6,314,325 B1 | 11/2001 | Fitz |
| 6,319,241 B1 | 11/2001 | King et al. |
| 6,349,233 B1 | 2/2002 | Adams |
| 6,353,762 B1 | 3/2002 | Baudino et al. |
| 6,356,786 B1 | 3/2002 | Rezai et al. |
| 6,360,750 B1 | 3/2002 | Gerber et al. |
| 6,366,814 B1 | 4/2002 | Boveja et al. |
| 6,393,325 B1 | 5/2002 | Mann et al. |
| 6,413,255 B1 | 7/2002 | Stern |
| 6,425,887 B1 | 7/2002 | McGuckin et al. |
| 6,438,423 B1 | 8/2002 | Rezai et al. |
| 6,440,090 B1 | 8/2002 | Schallhorn |
| 6,466,821 B1 | 10/2002 | Pianca et al. |
| 6,493,588 B1 | 12/2002 | Malaney et al. |
| 6,510,347 B2 | 1/2003 | Borkan |
| 6,512,958 B1 | 1/2003 | Swoyer et al. |
| 6,516,227 B1 | 2/2003 | Meadows et al. |
| 6,517,542 B1 | 2/2003 | Papay et al. |
| 6,522,926 B1 | 2/2003 | Kieval et al. |
| 6,535,767 B1 | 3/2003 | Kronberg |
| 6,582,441 B1 | 6/2003 | He et al. |
| 6,587,725 B1 | 7/2003 | Durand et al. |
| 6,605,094 B1 | 8/2003 | Mann et al. |
| 6,606,521 B2 | 8/2003 | Paspa et al. |
| 6,611,715 B1 | 8/2003 | Boveja |
| 6,625,496 B1 | 9/2003 | Ollivier |
| 6,638,276 B2 | 10/2003 | Sharkey et al. |
| 6,658,302 B1 | 12/2003 | Kuzma et al. |
| 6,714,822 B2 | 3/2004 | King et al. |
| 6,745,079 B2 * | 6/2004 | King ........................ 607/117 |
| 6,748,276 B1 | 6/2004 | Daignault, Jr. et al. |
| 6,754,539 B1 | 6/2004 | Erickson et al. |
| 6,788,975 B1 | 9/2004 | Whitehurst et al. |
| 6,792,318 B2 | 9/2004 | Chitre et al. |
| 6,832,115 B2 | 12/2004 | Borkan |
| 6,835,194 B2 | 12/2004 | Johnson et al. |
| 6,839,588 B1 | 1/2005 | Rudy |
| 6,849,075 B2 | 2/2005 | Bertolero et al. |
| 6,862,479 B1 | 3/2005 | Whitehurst et al. |
| 6,871,099 B1 | 3/2005 | Whitehurst et al. |
| 6,873,342 B2 | 3/2005 | Perry et al. |
| 6,889,094 B1 | 5/2005 | Kuzma et al. |
| 6,901,287 B2 | 5/2005 | Davis et al. |
| 6,902,547 B2 | 6/2005 | Aves et al. |
| 6,909,917 B2 | 6/2005 | Woods et al. |
| 6,928,320 B2 | 8/2005 | King |
| 6,971,391 B1 | 12/2005 | Wang et al. |
| 6,978,180 B2 | 12/2005 | Tadlock |
| 7,047,082 B1 | 5/2006 | Schrom et al. |
| 7,096,070 B1 | 8/2006 | Jenkins et al. |
| 7,127,287 B2 | 10/2006 | Duncan et al. |
| 7,181,289 B2 | 2/2007 | Pflueger et al. |
| 7,333,857 B2 | 2/2008 | Campbell |
| 7,337,005 B2 | 2/2008 | Kim et al. |
| 7,337,006 B2 | 2/2008 | Kim et al. |
| 7,447,546 B2 | 11/2008 | Kim et al. |
| 7,450,993 B2 | 11/2008 | Kim et al. |
| 7,502,651 B2 | 3/2009 | Kim et al. |
| 7,580,753 B2 | 8/2009 | Kim et al. |
| 2001/0003799 A1 | 6/2001 | Boveja |
| 2001/0006967 A1 | 7/2001 | Crain et al. |
| 2002/0064841 A1 | 5/2002 | Klemic et al. |
| 2002/0077684 A1 | 6/2002 | Clemens et al. |
| 2002/0087113 A1 | 7/2002 | Hartlaub |
| 2002/0099430 A1 | 7/2002 | Verness |
| 2002/0116030 A1 | 8/2002 | Rezai |
| 2002/0128694 A1 | 9/2002 | Holsheimer |
| 2002/0147486 A1 | 10/2002 | Soukup et al. |
| 2002/0198527 A1 | 12/2002 | Muckter |
| 2003/0018367 A1 | 1/2003 | Dilorenzo |
| 2003/0023241 A1 | 1/2003 | Drewry et al. |
| 2003/0045919 A1 | 3/2003 | Swoyer et al. |
| 2003/0069569 A1 | 4/2003 | Burdette et al. |
| 2003/0078633 A1 | 4/2003 | Firlik et al. |
| 2003/0088301 A1 | 5/2003 | King |
| 2003/0100933 A1 | 5/2003 | Ayal et al. |
| 2003/0114905 A1 | 6/2003 | Kuzma |
| 2003/0130577 A1 | 7/2003 | Purdy et al. |
| 2003/0144657 A1 | 7/2003 | Bowe et al. |
| 2003/0144709 A1 | 7/2003 | Zabara et al. |
| 2003/0181958 A1 | 9/2003 | Dobak, III |
| 2003/0187490 A1 | 10/2003 | Gliner |
| 2003/0195602 A1 | 10/2003 | Boling |
| 2003/0220677 A1 | 11/2003 | Doan et al. |
| 2004/0015202 A1 | 1/2004 | Chandler et al. |
| 2004/0019359 A1 | 1/2004 | Worley et al. |
| 2004/0019369 A1 | 1/2004 | Duncan et al. |
| 2004/0059404 A1 | 3/2004 | Bjorklund et al. |
| 2004/0116977 A1 | 6/2004 | Finch et al. |
| 2004/0122360 A1 | 6/2004 | Waldhauser et al. |
| 2004/0122477 A1 | 6/2004 | Whitehurst et al. |
| 2004/0122497 A1 | 6/2004 | Zhang et al. |
| 2004/0122498 A1 | 6/2004 | Zhang et al. |
| 2004/0147992 A1 | 7/2004 | Bluger et al. |
| 2004/0172089 A1 | 9/2004 | Whitehurst et al. |
| 2004/0210290 A1 | 10/2004 | Omar-Pasha |

(56) References Cited

U.S. PATENT DOCUMENTS

| | | |
|---|---|---|
| 2004/0215286 A1 | 10/2004 | Stypulkowski |
| 2004/0230273 A1 | 11/2004 | Cates et al. |
| 2004/0230280 A1 | 11/2004 | Cates et al. |
| 2004/0243210 A1 | 12/2004 | Morgan et al. |
| 2005/0027338 A1 | 2/2005 | Hill |
| 2005/0033295 A1 | 2/2005 | Wisnewski |
| 2005/0033393 A1 | 2/2005 | Daglow |
| 2005/0038489 A1 | 2/2005 | Grill |
| 2005/0060006 A1* | 3/2005 | Pflueger et al. .......... 607/43 |
| 2005/0070982 A1 | 3/2005 | Heruth et al. |
| 2005/0080325 A1 | 4/2005 | Erickson |
| 2005/0090885 A1 | 4/2005 | Harris et al. |
| 2005/0096718 A1 | 5/2005 | Gerber et al. |
| 2005/0149154 A1 | 7/2005 | Cohen et al. |
| 2005/0154437 A1 | 7/2005 | Williams |
| 2005/0159799 A1 | 7/2005 | Daglow et al. |
| 2005/0203599 A1 | 9/2005 | Garabedian et al. |
| 2005/0222647 A1 | 10/2005 | Wahlstrand et al. |
| 2005/0251237 A1 | 11/2005 | Kuzma et al. |
| 2006/0004364 A1 | 1/2006 | Green et al. |
| 2006/0009820 A1 | 1/2006 | Royle |
| 2006/0041295 A1 | 2/2006 | Osypka |
| 2006/0052827 A1 | 3/2006 | Kim et al. |
| 2006/0052836 A1* | 3/2006 | Kim et al. ............ 607/48 |
| 2006/0052856 A1 | 3/2006 | Kim et al. |
| 2006/0064150 A1 | 3/2006 | Heist et al. |
| 2006/0089609 A1 | 4/2006 | Bleich et al. |
| 2006/0089696 A1 | 4/2006 | Olsen et al. |
| 2006/0094976 A1 | 5/2006 | Bleich |
| 2006/0095088 A1 | 5/2006 | DeRidder |
| 2006/0155344 A1 | 7/2006 | Rezai et al. |
| 2006/0161235 A1 | 7/2006 | King |
| 2006/0167525 A1 | 7/2006 | King |
| 2006/0195169 A1 | 8/2006 | Gross et al. |
| 2006/0200121 A1 | 9/2006 | Mowery |
| 2006/0206118 A1 | 9/2006 | Kim et al. |
| 2006/0241716 A1 | 10/2006 | Finch et al. |
| 2006/0247750 A1 | 11/2006 | Seifert et al. |
| 2007/0043400 A1 | 2/2007 | Donders et al. |
| 2007/0060954 A1 | 3/2007 | Cameron et al. |
| 2007/0123954 A1 | 5/2007 | Gielen et al. |
| 2007/0179579 A1 | 8/2007 | Feler et al. |
| 2007/0213671 A1 | 9/2007 | Hiatt |
| 2007/0255366 A1 | 11/2007 | Gerber et al. |
| 2007/0270928 A1 | 11/2007 | Erlebacher |
| 2007/0276319 A1 | 11/2007 | Betts |
| 2008/0009927 A1 | 1/2008 | Vilims |
| 2008/0033431 A1 | 2/2008 | Jung et al. |
| 2008/0039916 A1 | 2/2008 | Colliou et al. |
| 2008/0103572 A1 | 5/2008 | Gerber |
| 2008/0103579 A1 | 5/2008 | Gerber |
| 2008/0103580 A1 | 5/2008 | Gerber |
| 2008/0119711 A1 | 5/2008 | Nikumb et al. |
| 2008/0140152 A1 | 6/2008 | Imran et al. |
| 2008/0140153 A1 | 6/2008 | Burdulis |
| 2008/0140169 A1 | 6/2008 | Imran |
| 2008/0147156 A1* | 6/2008 | Imran ............ 607/117 |
| 2008/0154349 A1 | 6/2008 | Rossing et al. |
| 2008/0167698 A1 | 7/2008 | Kim et al. |
| 2008/0183221 A1 | 7/2008 | Burdulis |
| 2008/0183257 A1 | 7/2008 | Imran et al. |
| 2008/0188916 A1 | 8/2008 | Jones et al. |
| 2009/0204173 A1 | 8/2009 | Fang et al. |
| 2009/0210041 A1 | 8/2009 | Kim et al. |
| 2009/0248095 A1 | 10/2009 | Schleicher et al. |
| 2009/0270960 A1* | 10/2009 | Zhao et al. ............ 607/117 |
| 2009/0299444 A1 | 12/2009 | Boling |
| 2010/0121408 A1 | 5/2010 | Imran et al. |
| 2010/0191307 A1 | 7/2010 | Fang et al. |
| 2011/0184486 A1 | 7/2011 | De Ridder |
| 2011/0257693 A1 | 10/2011 | Burdulis |
| 2011/0276056 A1 | 11/2011 | Grigsby et al. |
| 2012/0158094 A1 | 6/2012 | Kramer et al. |
| 2012/0283697 A1 | 11/2012 | Kim et al. |
| 2012/0310140 A1 | 12/2012 | Kramer et al. |

FOREIGN PATENT DOCUMENTS

| | | |
|---|---|---|
| CN | 101678204 A | 3/2010 |
| EP | 0779080 A | 6/1997 |
| EP | 1304135 A2 | 4/2003 |
| EP | 2756864 A1 | 7/2014 |
| JP | 03041191 B2 | 6/1991 |
| JP | H06-218064 A | 8/1994 |
| JP | 8500996 A | 2/1996 |
| JP | 8080353 A | 3/1996 |
| JP | 10243954 A | 9/1998 |
| JP | 2004512105 | 4/2004 |
| JP | 2006523215 | 10/2004 |
| JP | 2005516697 | 6/2005 |
| JP | 2006508768 | 3/2006 |
| JP | 2008526299 | 7/2008 |
| JP | 2009539425 A | 11/2009 |
| JP | 2009539426 A | 11/2009 |
| WO | WO 02/096512 A1 | 12/2002 |
| WO | WO 03/018113 A1 | 3/2003 |
| WO | WO 03/043690 A1 | 5/2003 |
| WO | WO 03/063692 | 8/2003 |
| WO | WO 03/066154 A2 | 8/2003 |
| WO | WO 03/084433 A2 | 10/2003 |
| WO | WO 03/090599 A2 | 11/2003 |
| WO | WO 2005/092432 A1 | 10/2005 |
| WO | WO 2006/033039 A1 | 3/2006 |
| WO | WO 2006/084635 A2 | 8/2006 |
| WO | WO 2008/094952 A2 | 8/2008 |
| WO | WO 2009/134350 A2 | 11/2009 |

OTHER PUBLICATIONS

Biology Online, http://www.biology-online.org/dictionary/Dorsal_root_ganglion.*

Mayfield Clinic for Brain & Spine http://www.mayfieldclinic.com/PE-AnatSpine.htm.*

MedicineNet.com Definition of Lateral http://www.medterms.com/script/main/art.asp?articlekey=6226.*

Abdulla et al.; Axotomy- and autotomy-induced changes in the excitability of rat dorsal root ganglion neurons; J Neurophysiol; 85(2); pp. 630-643; Feb. 2001.

Advanced Neuromodulation Systems, Inc. (ANSI) Research Briefing dated Aug. 20, 2004 by Stephens Inc. Investment Bankers pp. 1-4.

Advanced Neuromodulation Systems, Inc. (ANSI) Research Bulletin dated Jul. 2, 2004 by Stephens Inc. Investment Bankers pp. 1-7.

Advanced Neuromodulation Systems, Inc. (ANSI) Research Bulletin dated Jul. 27, 2004 by Stephens Inc. Investment Bankers pp. 1-9.

Advanced Neuromodulation Systems, Inc. Equity Research dated Jan. 16, 2003 by Pacific Growth Equities pp. 1-8.

Alo, Kenneth M. 2002. New Trends in Neuromodulation for the Management of Neuropathic Pain. Neurosurgery. 50 (4): 690-703.

Aoki, Yasuchika et al. 2004. Distribution and Immunocytochemical Characterization of Dorsal Root Ganglion Neurons Innervating the Lumbar Intervertebral Disc in Rats: A Review. Life Sciences. 74 (21): 2627-2642.

Askar, Zahid, et al. 2003. Scott Wiring for Direct Repair of Lumbar Spondylolysis. Spine. 28 (4): 354-357.

Baba, Hiroshi et al. 1999. Peripheral Inflammation Facilitates A? Fiber-Mediated Synaptic Input to the Substantia Gelatinosa of the Adult Rat Spinal Cord. The Journal of Neuroscience. 19 (2): 859-867.

Bajwa, Zahid H. et al. 2001. Herpetic Neuralgia: Use of Combination Therapy for Pain Relief in Acute and Chronic Herpes Zoster. Geriatrics. 56 (12): 18-24.

Barendse, G.A. et al. 2001. Randomized Controlled Trial of Percutaneo Intradiscal Radiofrequency Thermocoagulation for Chronic Discogenic Back Pain: Lack of Effect From a 90-Second 70 C Lesion. Spine. 26 (3): 287-92. (Abstract Only).

Barlocher, C.B. et al. 2003. Kryorhizotomy: An Alternative Technique for Lumbar Medial Branch Rhizotomy in Lumbar Facet Syndrome. J Neurosurg. 98 (1): 14-20. (Abstract Only).

Blau, A. et al. 1997. Characterization and Optimization of Microelectrode Arrays for In Vivo Nerve Signal Recording and Stimulation. Biosens Bioelectron.12 (9-10): 883-92. (Abstract Only).

(56) References Cited

OTHER PUBLICATIONS

Boston Scientific A Neuromodulation Primer dated Jun. 9, 2004 in Medical Supplies and Devices, published by Susquehanna Financial Group, LLLP pp. 1-17.
Brammah, T.B. et al. 1994. Syringomyelia as a Complication of Spinal Arachnoiditis. Spine. 19 (22): 2603-5. (Abstract Only).
Braverman D.L. et al. 2001. Using Gabapentin to Treat Failed Back Surgery Syndrome Caused by Epidural Fibrosis: A Report of 2 Cases. Arch Phys Med Rehabil. 82 (5): 691-3. (Abstract Only).
Burton et al.; The organization of the seventh lumbar spinal ganglion of the cat; J Comp Neurol.; 149(2); pp. 215-232; May 15, 1973.
Carlton, Susan M. et al. 2001. Tonic Control of Peripheral Cutaneo Nociceptors by Somatostatin Receptors. Journal of Neuroscience. 21 (11): 4042-4049.
Chaplan, S.R. et al. 1994. Quantitative Assessment of Tactile Allodynia in the Rat Paw. Journal of Neuroscience Methods. 53 (1): 55-63.
Cho, J. 1997. Percutaneo Radiofrequency Lumbar Facet Rhizotomy in Mechanical Low Back Pain Syndrome. Stereotact Funct Neurosurg. 68 (1-4): 212-7. (Abstract Only).
Crampon, M.-A. et al. 2002. Nerve Cuff Electrode With Shape Memory Alloy Armature: Design and Fabrication. Bio-Medical Materials and Engineering. 12 (4): 397-410.
Cuoco, Jr., Frank A. et al. 2000. Measurement of External Pressures Generated by Nerve Cuff Electrodes. IEEE Transactions on Rehabilitation Engineering. 8 (1): 35-41.
Cyberonics, Inc. Equity Research dated Jan. 16, 2003 by Pacific Growth Equities pp. 1-14.
Denny, N.M. et al. 2003. Evaluation of an Insulated Tuohy Needle System for the Placement of Interscalene Brachial Plex Catheters. Anaesthesia. 58 (6): 554-7. (Abstract Only).
Dreyfuss, Paul et al. 2000. Efficacy and Validity of Radiofrequency Neurotomy for Chronic Lumbar Zygapophysial Joint Pain. Spine. 25 (10): 1270-1277.
Dubuisson, D. 1995. Treatment of Occipital Neuralgia by Partial Posterior Rhizotomy at C1-3. J Neurosurg. 82 (4): 581-6. (Abstract Only).
Eschenfelder, Sebastian et al. 2000. Dorsal Root Section Elicits Signs of Neuropathic Pain Rather than Reversing Them in Rats With L5 Spinal Nerve Injury. Pain. 87 (2): 213-219.
Firth, Ava et al. 1999. Development of a Scale to Evaluate Postoperative Pain in Dogs. J Am Vet Med Assoc. 214 (5): 651-659.
Garcia Cosamalon, P. J. et al. 1991. Dorsal Percutaneo Radiofrequency Rhizotomy Guided With CT Scan in Intercostal Neuralgias. Technical note. Acta Neurochir (Wien). 109 (3-4): 140-1.
Giorgi, C. et al. 1984. Surgical Treatment of Glossopharyngeal Neuralgia and Pain From Cancer of the Nasopharynx. A 20-Year Experience. J Neurosurg. 61 (5): 952-5. (Abs. Only).
Gocer, A.I. et al. 1997. Percutaneo Radiofrequency Rhizotomy of Lumbar Spinal Facets the Results of 46 cases. Neurosurg Rev. 20 (2): 114-6. (Abstract Only).
Herron, L.D. 1989. Selective Nerve Root Block in Patient Selection for Lumbar Surgery: Surgical Results. J Spinal Disord. 2 (2): 75-9. (Abstract Only).
Higuchi, Yoshinori, et al. 2002. Exposure of the Dorsal Root Ganglion in Rats to Pulsed Radiofrequency Currents Activates Dorsal Horn Lamina I and II Neurons. Neurosurgery. 50 (4): 850-856.
Holsheimer, J. et al. 1995. Effects of Electrode Geometry and Combination on Nerve Fibre Selectivity in Spinal Cord Stimulation. Medical & Biological Engineering & Computing. 33 (5): 676-682.
Igarashi, T. et al. 2004. Lysis of Adhesions and Epidural Injection of Steroid/Local Anaesthetic During Epiduroscopy Potentially Alleviate Low Back and Leg Pain in Elderly Patients With Lumbar Spinal Stenosis. British Journal of Anaesthesia. 93 (2): 181-.
Julius, David et al. 2001. Molecular Mechanisms of Nociception. Nature. 413 (6852): 203-210.
Kanpolat, Yucel et al. 2001. Percutaneo Controlled Radiofrequency Trigeminal Rhizotomy for the Treatment of Idiopathic Trigeminal Neuralgia: 25-Year Experience with 1600 Patients. Neurosurgery. 48 (3): 524-534.
Kapadia, N.P. et al. 2000. Gabapentin for Chronic Pain in Spinal Cord Injury: A Case Report. Arch Phys Med Rehabil. 81 (10): 1439-41. (Abstract Only).
Kapoor, Vibhu et al. 2003. Refractory Occipital Neuralgia: Preoperative Assessment With CT-Guided Nerve Block Prior to Dorsal Cervical Rhizotomy. American Journal of Neuroradiology. 24 (10): 2105-10.
Karat, Laszlo et al. 2004. Deletion of Vanilloid Receptor 1-Expressing Primary Afferent Neurons for Pain Control. Journal of Clinical Investigation. 113 (9): 1344-1352.
Kline, David G. et al. 1998. Management and Results of Sciatic Nerve Injuries: a 24-Year Experience. Journal of Neurosurgery. 89 (1): 13-23.
Kobayashi, Shigeru et al. 2004. Pathology of Lumbar Nerve Root Compression Part 1: Intraradicular Inflammatory Changes Induced by Mechanical Compression. Journal of Orthopaedic Research. 22 (1): 170-179.
Kobayashi, Shigeru et al. 2004. Pathology of Lumbar Nerve Root Compression Part 2: Morphological and Immunohistochemicak Changes of Dorsal Root Ganglion. Journal of Orthopaedic Research. 22(1): 180-188.
Kocsis et al.; NR2B receptors are involved in the mediation of spinal segmental reflex potentials but not in the cumulative motoneuronal depolarization in vitro; Brain Research Bulletin, Elsevier Science Ltd.; vol. 64; No. 2; pp. 133-138; Aug. 30, 2004.
Koszewski, W. et al. 2003. [The DREZ Lesion as an Effective Treatment for Chronic Hypothetically Post-Herpetic Neuropathic Pain. Case Report and Review of Literature]. Neurol Neurochir Pol. 37 (4): 943-53. (Abstract Only).
Lawrence, Stephen M. et al. 2002. Long-Term Biocompatibility of Implanted Polymer-Based Intrafascicular Electrodes. Journal of Biomedical Materials Research. 63 (5): 501-506.
Lee, In-Seop et al. 2002. Characterization of Iridium Film as a Stimulating Neural Electrode. Biomaterials. 23 (11): 2375-2380.
Lew, Henry L. et al. 2004. Preganglionic Approach to Transforaminal Epidural Steroid Injections. Am. J. Phys. Med. Rehabil. 83 (5): 378.
Lopez et al.; Excitatory and inhibitory effects of serotonin on spinal nociceptive reflexes are mediated by 5-HT2 and 5-HT1B receptors; (Database Biosis Biosciences information service, Philadelphia, PA, US, XP002567533, accession No. PREV200100573757); Abstract; 2001.
Ma et al.; Enhanced excitability of dissociated primary sensory neurons after chronic compression of the dorsal root ganglion in the rat; Pain; 113(1-2); pp. 106-112; Jan. 2005.
Maher, C.O. et al. 1999. Lateral Exit-Zone Stenosis and Lumbar Radiculopathy. J Neurosurg. 90 (1): 52-8. (Abstract Only).
Mailley, Sophie et al. 2004. Thin Film Platinum Cuff Electrodes for Neurostimulation: In Vitro Approach of Safe Neurostimulation Parameters. Bioelectrochemistry. 63: 359-364.
Masini, Michelle et al. 1996. Activated Pyrolytic Carbon Tip Pacing Leads: An Alternative to Steroid-Eluting Pacing Leads? PACE. 1: 1832-1835.
Medtronic, Inc. Equity Research dated Dec. 18, 2002 by Pacific Growth Equities pp. 1-20.
Medtronic. Analysis of Sales/Earnings-F1Q05: Many Gives and Takes in the Quarter dated Aug. 20, 2004 by Morgan Stanley pp. 1-25.
Methods of Placement of Neurostimulation Lead, Infusion, Catheter, and/or Sensor Via Peripheral Vasculature. From IP.com PriorArtDatabase—Apr. 10, 2003—#000012136 http://www.priorartdatabase.com/IPCOM/000012136.
Modern Ideas: The Gate Control Theory of Chronic Pain. Spine-Health.com: Your Comprehensive Resource for Back Pain. http://www.spine-health.com/topics/cd/pain/chronic_pain_theories/chronic_pain_theory02.html (accessed Feb. 24, 2006).
Mond, Harry G. et al. 2004. Implantable Transveno Pacing Leads: The Shape of Things to Come. PACE. 27: 887-893.
Monti, Enrico. 2004. Peripheral Nerve Stimulation: A Percutaneo Minimally Invasive Approach. Neuromodulation. 7 (3): 193. (Abstract Only).
Myles et al.; Effects of different methods of peripheral nerve repair on the number and distribution of muscle afferent neurons in rat dorsal root ganglion; J Neurosurg; 77(3); pp. 457-462; Sep. 1992.

(56) References Cited

OTHER PUBLICATIONS

Nannini et al.; Muscle recruitment with intrafascicular electrodes; IEEE Trans on Biomedical Engineering; vol. 38; No. 8; pp. 769-776 Aug. 1991.
Naples, Gregory G. 1988. A Spiral Nerve Cuff Electrode for Peripheral Nerve Stimulation. IEEE Transactions on Biomedical Engineering. 35 (11): 905-916.
Narozny, Martin et al. 2001. Therapeutic Efficacy of Selective Nerve Root Blocks in the Treatment of Lumbar Radicular Leg Pain. Swiss Med Wkly. 131 (5-6): 75-80.
Nashold, Blaine S. et al. 1979. Peripheral Nerve Stimulation for Pain Relief Using a Multicontact Electrode System. Technical note. Journal of Neurosurgery. 51 (6): 872-873.
Nashold, Blaine S. et al. 1982. Long-Term Pain Control by Direct Peripheral-Nerve Stimulation. The Journal of Bone and Joint Surgery. 64 (1): 1-10.
Neumann, Simona et al. 2002. Regeneration of Sensory Axons Within the Injured Spinal Cord Induced by Intraganglionic cAMP Elevation. Neuron. 34 (6): 885-93.
Nielson, K.D. et al. 1976. Peripheral Nerve Injury From Implantation of Chronic Stimulating Electrodes for Pain Control. Surg Neurol. 5 (1): 51-3. (Abstract Only).
North, Richard B. et al. 1991. Dorsal Root Ganglionectomy for Failed Back Surgery Syndrome: A 5-Year Follow-Up Study. J Neurosurg. 74: 236-242.
North, Richard B. et al. 2000. Chapter 123: Current Concepts in the Neurosurgical Management of Persistent Pain (pp. 1634-1637). Operative Neurosurgical Techniques 4th Edition (Henry H. Schmidek et al. eds.). Philadelphia: W.B. Saunders Company.
Nygaard, Oystein P. et al. 1998. The Function of Sensory Nerve Fibers in Lumbar Radiculopathy: Use of Quantitative Sensory Testing in the Exploration of Different Populations of Nerve Fibers and Dermatomes. Spine. 23 (3): 348-352.
Obata, K. et al. 2004. Activation of Extracellular Signal-Regulated Protein Kinase in the Dorsal Root Ganglion Following Inflammation Near the Nerve Cell Body. Neuroscience. 126 (4): 1011-1021.
Obata, Koichi, et al. 2002. Expression of Neurotrophic Factors in the Dorsal Root Ganglion in a Rat Model of Lumbar Disc Herniation. Pain. 99 (1-2): 121-132.
Olby, Natasha J. et al. 2001. Development of a Functional Scoring System in Dogs With Acute Spinal Cord Injuries. Am J Vet Res. 62 (10): 1624-1628.
Parlier-Cuau, Caroline et al. 1999. Symptomatic Lumbar Facet Joint Synovial Cysts: Clinical Assessment of Facet Joint Steroid Injection After 1 and 6 Months and Long-Term Follow-Up in 30 Patients. Radiology. 210 (2): 509-513.
Pedrolli, C. et al. 1990. [Dorsolumbar Arachnoid Cysts. A Case Report]. Recenti Prog Med. 81 (11): 699-701. (Abstract Only).
Prats-Galino et al.; Representations of hindlimb digits in rat dorsal root ganglia; J Comp Neurol; 408(1); pp. 137-145; May 24, 1999.
Rodriguez, Francisco J. et al. 2000. Polyimide Cuff Electrodes for Peripheral Nerve Stimulation. Journal of Neuroscience Methods. 98 (2): 105-118.
Rokugo, Tomoyuki et al. 2002. A Histochemical Study of Substance P in the Rat Spinal Cord: Effect of Transcutaneo Electrical Nerve Stimulation. J Nippon Med Sch. 69 (5): 428-433.
Romero, E. et al. 2001. Neural Morphological Effects of Long-Term Implantation of the Self-Sizing Spiral Cuff Nerve Electrode. Medical & Biological Engineering & Computing. 39 (1): 90-100.
Rongstad, K. et al. 1996. Popliteal Sciatic Nerve Block for Postoperative Analgesia. Foot Ankle Int. 17 (7): 378-82. (Abstract Only).
Ruetten, S. et al. 2003. Endoscopic Surgery of the Lumbar Epidural Space (Epiduroscopy): Results of Therapeutic Intervention in 93 Patients. Minim Invasive Neurosurg. 46 (1): 1-4. (Abstract Only).
Sairyo, K. et al. 2003. A New Endoscopic Technique to Decompress Lumbar Nerve Roots Affected by Spondylolysis. Technical Note. J Neurosurg. 98 (3): 290-3. (Abstract Only).
Salame, K. et al. 2003. Surgical Treatment of Spasticity by Selective Posterior Rhizotomy 30 Years Experience. Isr Med Assoc J. 5 (8): 543-6. (Abstract Only).
Saris, S.C. et al. 1986. Sacrococcygeal Rhizotomy for Perineal Pain. Neurosurgery. 19 (5): 789-93. (Abstract Only).
Sauvage, P.J. et al. 2000. Intraspinal Synovial Cysts of the Lumbar Spine: Imaging Findings and Treatment by Percutaneo Steroid Injection. Review of 13 Cases. [Kystes Synoviaux Intraspinaux Lombaires: Imagerie et Traitement Par Infiltration. A Propos De.
Schwartzman, Robert J. et al. 2001. Neuropathic Central Pain: Epidemiology, Etiology, and Treatment Options. Arch Neurol. 58 (10): 1547-1550.
Sedan, R. et al. 1978. Therapeutic Electrical Neurostimulation. French Language Society of Neurosurgery—28th Annual Congress—Athens, May 29-30, 1978. Neurochirurgie. 24: 3-& Suppl. 1 (in French with English Summary pp. 121-125.
Sheth, Rishi N. et al. 2002. Mechanical Hyperalgesia After an L5 Ventral Rhizotomy or an L5 Ganglionectomy in the Rat. Pain. 96: 63-72.
Siddall, Philip J. et al. 2004. Persistent Pain as a Disease Entity: Implications for Clinical Management. Anesth Analg. 99: 510-20.
Silvers, H.R. 1990. Lumbar Percutaneo Facet Rhizotomy. Spine.15 (1): 36-40. (Abstract Only).
Slappendel, R. et al. 1997. The efficacy of Radiofrequency Lesioning of the Cervical Spinal Dorsal Root Ganglion in a Double Blinded Randomized Study: No difference Between 40 Degrees C and 67 Degrees C Treatments. Pain. 73 (2): 159-63. (Abstract Only).
Sluijter, Menno E. et al. 1998. The Effects of Pulsed Radiofrequency Fields Applied to the Dorsal Root Ganglion—A Preliminary Report. The Pain Clinic.11 (2): 109-117.
Smith, H.P. et al. 1981. Radiofrequency Neurolysis in a Clinical Model: Neuropathological Correlation. J Neurosurg. 55 (2): 246-53. (Abstract Only).
Spaic, M. et al. 1999. Drez Surgery on Con Medullaris (After Failed Implantation of Vascular Omental Graft) for Treating Chronic Pain Due to Spine (Gunshot) Injuries. Acta Neurochir(Wein). 141(12): 1309-1312.
Spaic, M. et al. 2002. Microsurgical DREZotomy for Pain of Spinal Cord and Cauda Equina Injury Origin: Clinical Characteristics of Pain and Implications for Surgery in a Series of 26 Patients. Acta Neurochir (Wien). 144 (5): 453-462.
Stanton-Hicks, M. et al. 1997. Stimulation of the Central and Peripheral Nervo System for the Control of Pain. Journal of Clinical Neurophysiology. 14 (1): 46-62.
Steinbok, P. et al. 1998. Complications After Selective Posterior Rhizotomy for Spasticity in Children With Cerebral Palsy. Pediatr Neurosurg. 28 (6): 300-13. (Abstract Only).
Stolker, Robert J. et al. 1994. The Treatment of Chronic Thoracic Segmental Pain by Radiofrequency Percutaneo Partial Rhizotomy. J Neurosurg. 80 : 986-992.
Strait, T.A. et al. 1981. Intraspinal Extradural Sensory Rhizotomy in Patients With Failure of Lumbar Disc Surgery. J Neurosurg. 54 (2): 193-6. (Abstract Only).
Taha, J.M. et al. 1995. Long-Term Results of Radiofrequency Rhizotomy in the Treatment of Cluster Headache. Headache. 35 (4): 193-6. (Abstract Only).
Taub, Arthur et al. 1995. Dorsal Root Ganglionectomy for Intractable Monoradicular Sciatica: A Series of 61 Patients. Stereotact Funct Neurosurg. 65 (1-4): 106-110.
Uematsu, Sumio. 1988. Chapter 106: Percutaneo Electrothermocoagulation of Spinal Nerve Trunk, Ganglion, and Rootlets (pp. 1207-1221). Operative Neurosurgical Techniques, Indications, Methods and Results 2nd edition. (Henry H. Schmidek et al. eds.). P.
Van Zundert, Jan et al. 2005. Pulsed Radiofrequency in Chronic Pain Management: Looking for the Best Use of Electrical Current. World Institute of Pain. 5 (2): 74-76.
Van De Kraats, Everine B. et al. 2004. Noninvasive Magnetic Resonance to Three-Dimensional Rotational X-Ray Registration of Vertebral Bodies for Image-Guided Spine Surgery. Spine. 29 (3): 293-297.
Van Kleef, M. et al. 1993. Effects and Side Effects of a Percutaneo Thermal Lesion of the Dorsal Root Ganglion in Patients with Cervical Pain Syndrome. Pain. 52 (1): 49-53.

(56) References Cited

OTHER PUBLICATIONS

Van Kleef, M. et al. 1996. Radiofrequency Lesion Adjacent to the Dorsal Root Ganglion for Cervicobrachial Pain: A Prospective Double Blind Randomized Study. Neurosurgery. 38 (6): 1127-31.
Van Kleef, Maarten et al. 1998. Chapter 160: Radiofrequency Lesions in the Treatment of Pain of Spinal Origin (pp. 1585-1599). Textbook of Stereotactic and Functional Neurosurgery 1st Edition. (Philip L. Gildenberg et al. eds.). New York: McGraw-Hill.
Van Zundert, J. et al. 2005. Pulsed and Continuo Radiofrequency Current Adjacent to the Cervical Dorsal Root Ganglion of the Rat Induces Late Cellular Activity in the Dorsal Horn. Anesthesiology. 102 (1): 125-31.
Vaughan, R. 1975. Percutaneo Radiofrequency Gangliotomy in the Treatment of Trigeminal Neuralgia and Other Facial Pain. Aust N Z J Surg. 45 (2): 203-7. (Abstract Only).
Viton, J.-M. et al. 1998. Short-Term Assessment of Periradicular Corticosteroid Injections in Lumbar Radiculopathy Associated With Disc Pathology. Neuroradiology. 40 (1): 59-62.
Viton, J.M. et al. 1998. Short-Term Evaluation of Periradicular Corticosteroid Injections in the Treatment of Lumbar Radiculopathy Associated With Disc Disease. Rev Rhum Engl Ed. 65 (3): 195-200. (Abstract Only).
Wagner, A.L. et al. 2002. Selective Nerve Root Blocks. Tech Vasc Intery Radiol. 5 (4): 194-200. (Abstract Only).
Waxman et al.; Sodium channels, excitability of primary sensory neurons, and the molecular basis of pain; Muscle Nerve; 22(9); pp. 1177-1187; Sep. 1999.
Weiner, Richard L. 2000. The Future of Peripheral Nerve Neurostimulation. Neurological Research. 22 (3): 299-304.
Weiner, Richard L. 2003. Peripheral Nerve Neurostimulation. Neurosurgery Clinics of North America. 14 (3): 401-408.
Weinstein, James et al. 1988. The Pain of Discography. Spine. 13 (12):1344-8.
Wessels et al.; A rostrocaudal somatotopic organization in the brachial dorsal root ganglia of neonatal rats; Clin Neurol Neurosurg; 95 Suppl; pp. S3-S11; 1993.
Wessels et al.; Evidence for a rostrocaudal organization in dorsal root ganglia during development as demonstrated by intra-uterine WGA-HRP injections into the hindlimb of rat fetuses; Brain Res Dev Brain Res; 54(2); pp. 273-281; Jul. 1, 1990.
Wessels et al.; Somatotopic organization in the sensory innervation of the rat hindlimb during development, using half dorsal root ganglia as subsegmental units; Eur J Morphol; 28(2-4); pp. 394-403; 1990.
Wessels et al.; The rostrocaudal organization in the dorsal root ganglia of the rat: a consequence of plexus formation?; Anat Embryol (Berl); 190(1); pp. 1-11; Jul. 1994.
Wetzel, F. Todd et al. 1997. Extradural Sensory Rhizotomy in the Management of Chronic Lumbar Radiculopathy: A Minimum 2-Year Follow-up Study. Spine. 22 (19): 2283-2291.
Wetzel, F.T. 1992. Chronic Benign Cervical Pain Syndromes: Surgical Considerations. Spine. 17 (10): S367-74. (Abstract Only).
Wetzel, F.T. et al. 1992. The Treatment of Chronic Extremity Pain in Failed Lumbar Surgery. The Role of Lumbar Sympathectomy. Spine. 17 (12): 2367-8. (Abstract Only).
White, P.F. et al. 2003. The Use of a Continuo Popliteal Sciatic Nerve Block After Surgery Involving the Foot and Ankle: Does It Improve the Quality of Recovery? Anesth Analg. 97 (5): 1303-9. (Abstract Only).
Whitworth, Louis Anthony et al. 2002. Application of Spinal Ablative Techniques for the Treatment of Benign Chronic Painful Conditions. Spine. 27 (22): 2607-2612.
Wilkinson, H.A. et al. 2001. Sensory Ganglionectomy: Theory, Technical Aspects, and Clinical Experience. J Neurosurg. 95 (1): 61-6. (Abstract Only).
Wong, C.B. et al. 2002. Clinical Outcomes of Revision Lumbar Spinal Surgery: 124 Patient With a Minimum of Two Years of Follow-Up. Chang Gung Med J. 25 (3): 175-82. (Abstract Only).
Wright, Robert E. et al. 1998. Neurostimulation of the L2 Dorsal Root Ganglion for Intractable Disc Pain: Description of a Novel Technique. Presented at the IFESS.
Wu, Gang et al. 2001. Early Onset of Spontaneo Activity in Uninjured C-Fiber Nociceptors After Injury to Neighboring Nerve Fibers. Journal of Neuroscience. 21 (8): RC140.
Yamashita, Toshihiko et al. 2002. A Quantitative Analysis of Sensory Function in Lumbar Radiculopathy Using Current Perception Threshold Testing. Spine. 27 (14): 1567-1570.
Yoshida, Hirotoshi et al. 1997. Lumbar Nerve Root Compression Caused by Lumbar Intraspinal Gas: Report of Three Cases. Spine.22 (3): 348-351.
Young, R.F. 1996. Chapter 161: Dorsal Rhizotomy and Dorsal Root Ganglionectomy (pp. 3442-3451). Neurological Surgery 4th Edition. (Julian R. Youmans ed.). Philadelphia: W.B. Saunders Company.
Imran et al.; U.S. Appl. No. 12/607,009 entitled "Selective stimulation systems and signal parameters for medical conditions," filed Oct. 27, 2009.
Linker et al.; U.S. Appl. No. 12/687,737 entitled "Stimulation leads, delivery systems and methods of use," filed Jan. 14, 2010.
Kishawi et al.; U.S. Appl. No. 12/730,908 entitled "Pain management with stimulation subthreshold to parasthesia," filed Mar. 24, 2010.
Kim et al.; U.S. Appl. No. 13/402,786 entitled "Neurostimulation System," filed Feb. 22, 2012.
Kramer et al.; U.S. Appl. No. 13/458,697 entitled "Selective stimulation to modulate the sympathetic nervous system," filed Apr. 27, 2012.
Haller, H. et al. Treatment of Chronic Neuropathic Pain After Traumatic Central Cervical Cord Lesion with Gabapentin. Journal of Neural Transmission. 110 (9): 977-981. Sep. 2003.
Kim et al.; U.S. Appl. No. 13/706,100 entitled "Neurostimulation Methods and Systems," filed Dec. 5, 2012.
Kishawi et al.; U.S. Appl. No. 13/753,326 entitled "Pain management with stimulation subthreshold to parasthesia," filed Jan. 29, 2013.
Wedley et al. Handbook of Clinical Techniques in the Management of Chronic Pain. Taylor & Francis; pp. 17-19. Nov. 27, 1996.
Cipolla—The Cerebral Circulation,Chap. 3—Perivascular Innervation ; Morgan & Claypool Life Sciences; San Rafael, Ca.; 1(1):pp. 3; Jan. 2009.
Truijen et al.; Parasympathetic control of blood flow to the activated human brain; Exp Physiol; 95(10):980-981; Oct. 2010.
Kim et al.; U.S. Appl. No. 14/216,805 entitled "Neurostimulation System," filed Mar. 17, 2014.
Burdulis; U.S. Appl. No. 13/975,083 entitled "Hard Tissue Anchors and Delivery Devices," filed Aug. 23, 2013.
Kishawi et al.; U.S. Appl. No. 14/615,281 entitled "Pain management with stimulation subthreshold to paresthesia," filed Feb. 5, 2015.
Imran; U.S. Appl. No. 14/633,046 entitled "Delivery devices, systems and methods for stimulating nerve tissue on multiple spinal levels," filed Feb. 26, 2015.
Burdulis; U.S. Appl. No. 14/633,060 entitled "Hard tissue anchors and delivery devices," filed Feb. 26, 2015.
Kramer; U.S. Appl. No. 14/362,543 entitled "Neuromodulation of subcellular structures within the dorsal root ganglion," filed Jun. 3, 2014.
Horsch, S. et al. Epidural spinal cord stimulation in the treatment of severe peripheral arterial occlusive disease; Annals of Vascular Surgery; 8(5): 468-74. Sep. 1994.
Clark, Robert K. "Anatomy and physiology: understanding the human body"; Jones & Bartlett Publishers; Sudbury, MA; ISBN 0-7637-4816-6; Chapter 12; pp. 213-215; Feb. 28, 2005.

\* cited by examiner

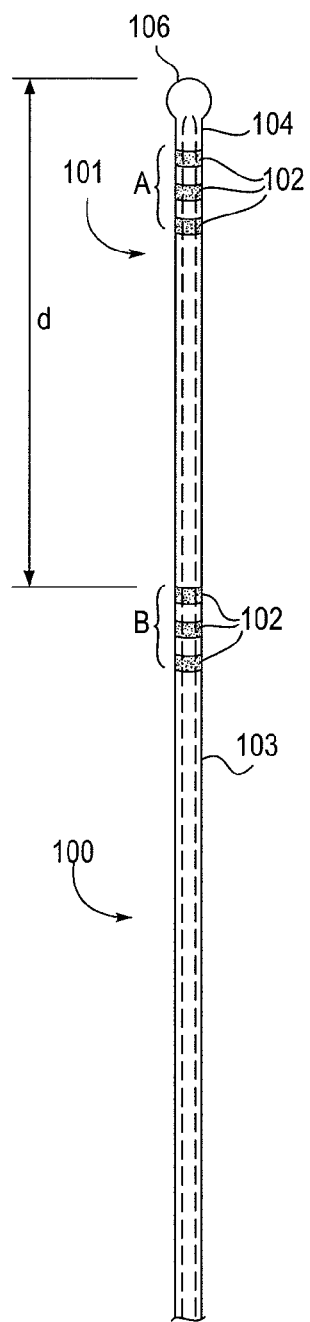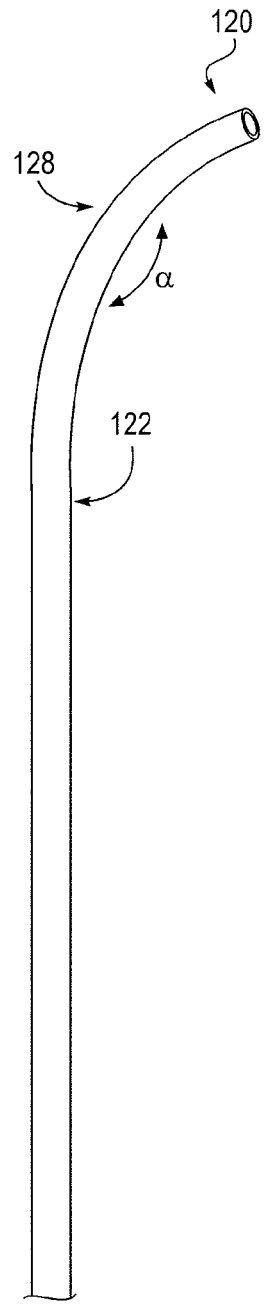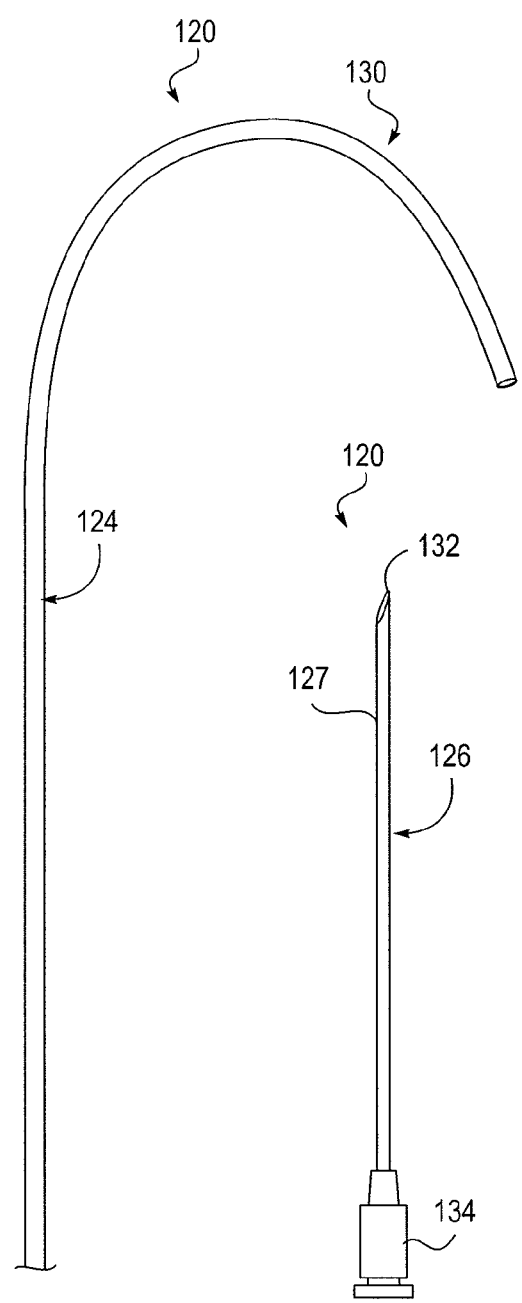
FIG. 6A    FIG. 6B    FIG. 6C    FIG. 6D

METHODS, SYSTEMS AND DEVICES FOR NEUROMODULATING SPINAL ANATOMY

CROSS-REFERENCES TO RELATED APPLICATION

This application claims priority under 35 U.S.C. 119(e) to U.S. Provisional Patent Application No. 61/178,847, entitled "Methods, Systems and Devices for Delivering Stimulation To Spinal Anatomy", filed May 15, 2009, which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Neuromodulation is a method of treating pain symptoms by therapeutically altering activity in pain pathways with the use of an implantable device. Neuromodulation works by either actively stimulating nerves to produce a natural biological response or by applying targeted pharmaceutical agents in small doses directly to a site of action.

Electrical stimulation involves the application of electrodes to the brain, the spinal cord or peripheral nerves of a patient. These precisely placed electrodes are typically mounted on a lead that is connected to a pulse generator and power source, which generates the necessary electrical stimulation. A low-voltage electrical current passes from the generator to the nerve, and can either inhibit pain signals or stimulate neural impulses where they were previously absent.

In the case of pharmacological agents delivered through implanted leads or catheters, the drug can be administered in smaller doses because it does not have to be metabolized and pass through the body before reaching the target area. Smaller doses—in the range of 1/300 of an oral dose—can mean fewer side effects, increased patient comfort and improved quality of life.

However, neuromodulation is not without its risks and complications. Many studies show that less than 50% of patients receive meaningful pain relief with spinal cord stimulation. Patients fail spinal cord stimulation for many reasons including unwanted stimulation, inability to stimulate the target area, and sometimes loss of stimulation over time. Likewise, unpleasant stimulation of the chest or rib area may occur due to undesirable positioning or movement of the stimulation lead. In addition, changes in stimulation may occur over time due to scar tissue forming around the leads, fracture of the lead, or movement of the lead position. For example, migration of the electrode may occur resulting in a loss or change of stimulation.

Many of these complications may be lessened or avoided with more desirable placement of the stimulation leads and a greater ability to maintain electrodes in such desirable position. In addition, surgical complications may be lessened or reduced with less invasive procedures. Further, such positioning of leads should be reversible without damaging or harming the patient anatomy, particularly delicate nerve tissue. Currently, approximately 20% to 40% of conventional spinal cord stimulation patients require revision or explantation of at least one lead. Therefore, such positioning should be reversible in the instance that removal or repositioning of a lead is desired for any reason. At least some of these objectives will be met by the present invention.

BRIEF SUMMARY OF THE INVENTION

The present invention provides devices, systems and methods for treating pain or other conditions while minimizing possible complications and side effects. Such devices, systems and methods are minimally invasive, therefore reducing possible complications resulting from the implantation procedure, and targeted so as to treat specific anatomy while minimizing or excluding effects on other nearby anatomies. Treatment typically includes electrical stimulation and/or delivery of pharmacological or other agents with the use of a lead or catheter. Examples herein will be described with the use of a lead providing electrical stimulation for illustration purposes, however it may be appreciated that the examples may utilize other types of neuromodulation. The present invention provides improved anchoring which reduces migration of the lead yet allows for easy repositioning or removal of the lead if desired. The present invention also includes devices, systems and methods of simultaneously treating multiple targeted anatomies. This shortens procedure time and allows for less access points, such as needle sticks to the epidural space, which in turn reduces complications, such as cerebral spinal fluid leaks, patient soreness and recovery time. Other possible complications related to the placement of multiple devices are also reduced.

In some embodiments, the dorsal root ganglion (DRG) is the target anatomy and the devices, systems and methods selectively stimulating one or more DRGs while minimizing or excluding undesired stimulation of other anatomies. This provides for management of pain sensations with minimal deleterious side effects, such as undesired motor responses. Stimulation of a target anatomy is achieved with the use of a lead having at least one electrode thereon.

In a first aspect of the present invention, a method is provided for positioning a lead comprising a shaft having a distal tip and at least one electrode disposed a distance along the shaft proximal to the distal tip. In some embodiments, the method comprises positioning the at least one electrode near a second dorsal root ganglion and positioning the distal tip near a first dorsal root ganglion by passing at least part of the distance along the shaft through a foramen associated with the second dorsal root ganglion.

In some embodiments, positioning the distal tip near the first dorsal root ganglion comprises wrapping at least a portion of the distance along the shaft around at least a portion of a pedicle. In some instances, such positioning further comprises passing the distal tip at least partially through a foramen associated with the first dorsal root ganglion.

Optionally, the method further comprises advancing the lead within an epidural space prior to the positioning steps. In other embodiments, the method further comprises advancing the lead within a sacrum prior to the positioning steps. In still other embodiments, the method further comprises advancing the lead extraforaminally toward the second dorsal root ganglion prior to the positioning steps.

In some instances the first and second dorsal root ganglia are on different spinal levels. The different spinal levels may be adjacent spinal levels or non-adjacent spinal levels. Or, the first and second dorsal root ganglia may be on the same spinal level.

In some embodiments, the lead includes an additional at least one electrode near the distal tip and wherein positioning the distal tip comprises positioning the additional at least one electrode near the first dorsal root ganglion.

In a second aspect of the present invention, a method is provided for positioning a lead comprising a shaft having a distal tip, the method comprising advancing the lead within an epidural space, moving the distal tip laterally outward from the epidural space through a foramen, and curving the distal tip back toward the epidural space so that a portion of the shaft wraps at least partially around a pedicle forming a border of the foramen. In some embodiments, the lead includes at least one electrode near the distal tip and another at least one electrode spaced a distance proximal to the distal tip, wherein the method includes positioning the at least one electrode near a first dorsal root ganglion and positioning the another at least one electrode near a second dorsal root ganglion corresponding with the foramen. In other embodiments, curving the distal tip further comprises curving the distal tip back toward the epidural space so that a portion of the shaft additionally wraps at least partially around another pedicle.

In a third aspect of the present invention, a method is provided for positioning a lead comprising a shaft having a distal tip, the method comprising advancing the lead within a sacrum, moving the distal tip from within the sacrum through a first foramen to outside of the sacrum, and passing the distal tip at least partially through a second foramen from outside the sacrum to within the sacrum. In some embodiments, the lead includes at least one electrode near the distal tip and another at least one electrode spaced a distance proximal to the distal tip, wherein the method includes positioning the at least one electrode near a first dorsal root ganglion and positioning the another at least one electrode near a second dorsal root ganglion. In other embodiments, advancing the lead within the sacrum includes entering the sacrum via a sacral hiatus.

In a fourth aspect of the present invention, a lead is provided for neuromodulating a first spinal tissue and a second spinal tissue within a body, the lead comprising a shaft having a distal tip, wherein the shaft is constructed to allow curving around at least a portion of a pedicle, a first grouping of electrodes disposed along the shaft proximal to the distal tip, and a second grouping of electrodes disposed along the shaft a distance proximally from the first grouping of electrodes, so that the distance between the groupings allows alignment of at least one of the first grouping of electrodes with the first spinal tissue on a first spinal level, curving of the shaft between the electrode groupings around at least a portion of the pedicle and alignment of at least one of the second grouping of electrodes with the second spinal tissue on a second spinal level.

In some embodiments, the first and second spinal levels are adjacent to each other. In other embodiments, the first and second spinal levels are not adjacent to each other.

In some embodiments, the first and/or second spinal tissues are dorsal root ganglia. In some embodiments, a portion of the shaft is configured for extending through a foramen prior to curving around at least a portion of the pedicle. Optionally, the portion of the shaft may further be configured for further extending through another foramen.

In some instances, the distance between the at least one first and second grouping of electrodes is in the range of approximately 30-65 mm. Optionally, the shaft may be sized to be advanced through an epidural needle. Or, the shaft may be configured to be advanced toward the first spinal tissue with an extraforaminal approach.

In some embodiments, the shaft has a stiffness which allows the curving by advancement of curved sheath thereover. In other embodiments, the first grouping of electrodes is disposed proximal to the distal tip by a length in the range of approximately ½, one, two, three, four, five, six or more spinal levels.

In a fifth aspect of the present invention, a method is provided of positioning a lead comprising a shaft having a first grouping of at least one electrode and a second grouping of at least one electrode disposed proximally to the first grouping along the shaft, the method comprising positioning the first grouping of at least one electrode near a first dorsal root ganglion, and positioning the second grouping of at least one electrode near a second dorsal root ganglion, wherein the first and second dorsal root ganglia are disposed on opposite sides of a spinal canal.

In some embodiments, the first and second dorsal root ganglia are disposed on a same spinal level. In other embodiments, the first and second dorsal root ganglia are disposed on different spinal levels.

In some embodiments, the method further comprises accessing the spinal canal with an epidural approach. Optionally, such a method may further comprise advancing the lead in an antegrade direction prior to positioning the first grouping of at least one electrode near the first dorsal root ganglion.

In some embodiments, the method further comprises accessing the spinal canal with an extraforaminal approach. In other embodiments, the method further comprises advancing the lead through at least one foramen.

Other objects and advantages of the present invention will become apparent from the detailed description to follow, together with the accompanying drawings.

BRIEF DESCRIPTION OF THE DRAWINGS

FIGS. 6A-6D illustrate one embodiment of a lead (FIG. 6A) and compatible delivery system 120 including a sheath 122 (FIG. 6B), stylet 124 (FIG. 6C) and introducing needle 126 (FIG. 6D).

DETAILED DESCRIPTION OF THE INVENTION

Figure 1A:
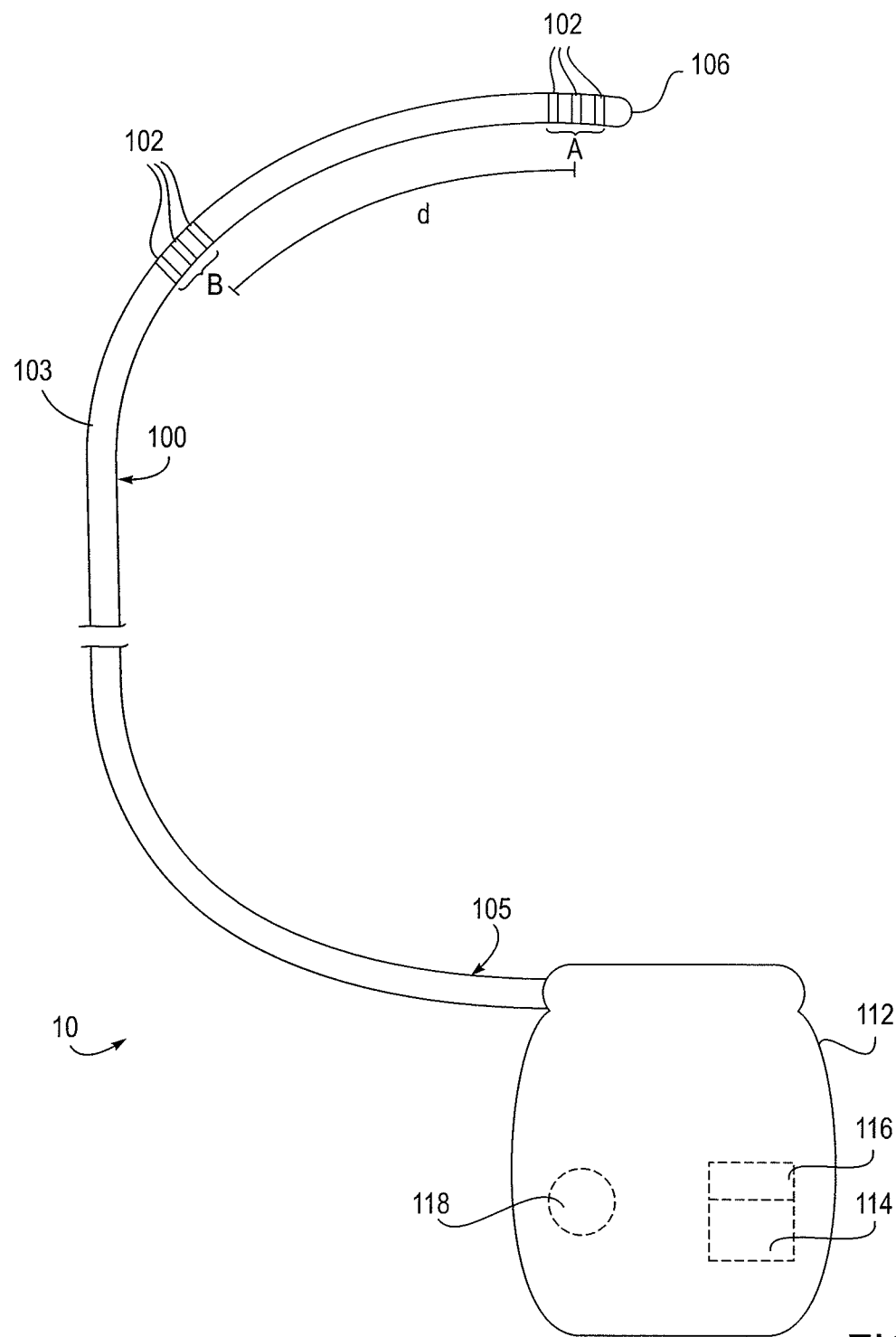
FIG. 1A illustrates an embodiment of a stimulation system of the present invention.

FIG. 1A illustrates an embodiment of a stimulation system 10 of the present invention, wherein the system 10 includes a lead 100, having at least one electrode 102 disposed thereon, and an implantable pulse generator (IPG) 112. The lead 100 comprises a shaft 103 having a proximal end 105 and a distal tip 106. The proximal end 105 is insertable into the IPG 112 to provide electrical connection to the lead 100. The IPG 112 contains a processor 114, programmable stimulation information in memory 116, as well as a power supply 118, e.g., a battery, so that once programmed and turned on, the IPG 112 can operate independently of external hardware. The IPG 112 is turned on and off and programmed to generate the desired stimulation pulses from an external programming device using transcutaneous electromagnetic or RF links. The stimulation information includes signal parameters such as voltage, current, pulse width, repetition rate, and burst rates.

In this embodiment, the at least one electrode 102 includes one or more electrodes 102 disposed near the distal tip 106 and one or more electrodes 102 spaced at least a distance d from the distal tip 106. In particular, in this embodiment, the at least one electrode 102 includes three electrodes disposed near the distal tip 106 (forming a first grouping A) and three electrodes disposed along the shaft 103 (forming a second grouping B). The first grouping A and second grouping B are spaced apart by a distance d. The distance d is significantly greater than the distance between the electrodes within each grouping. In this embodiment, the distance d is measured from the approximate centers of each grouping. The distance d allows for the first grouping A of electrodes 102 to reside near a first target anatomy and the second grouping B of electrodes 102 to reside near a second target anatomy. In some examples, the first target anatomy is a DRG on a first level and the second target anatomy is a DRG on a second level. The first and second levels may be adjacent to each other or may be spaced apart. The lead 100 may be positioned in a variety of arrangements to align the groupings A, B with the DRGs, such as will be described and illustrated herein. Such arrangements allow simultaneous treatment of multiple targeted anatomies thereby reducing possible complications related to the placement of multiple devices, including reducing the amount of radiation exposure to the patient and minimizing the amount of time in the operating room due to the reduction in devices being placed. In addition, such arrangements provide improved anchoring which reduces migration of the lead yet allows for easy repositioning or removal of the lead if desired.

Figure 1B:
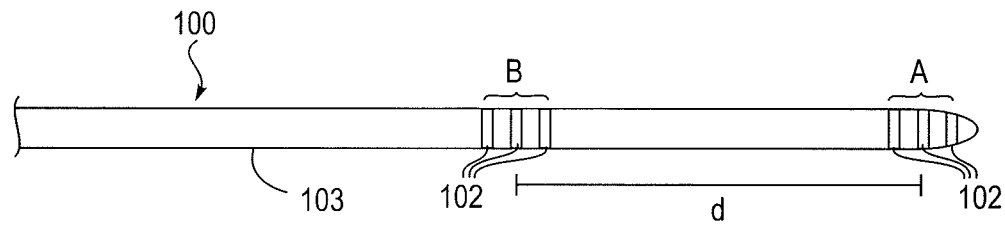
FIGS. 1B, 1C, 1D, 1E illustrate embodiments of leads of the present invention.

It may be appreciated that the system 10 may include any number of leads 100, including one, two, three, four, five, six seven, eight or more leads 100. Likewise, each lead 100 may include any number of electrodes 102, including one, two, three, four, five, six or more electrodes 102. Further, each lead 100 may include any number of electrode groupings. FIGS. 1B-1E illustrate a sampling of lead 100 embodiments having different arrangements of electrode groupings. FIG. 1B illustrates the lead 100 embodiment of FIG. 1A As described above, the first grouping A and second grouping B are spaced apart by a distance d which reflects the distance between target anatomies. In this embodiment, the distance d is measured from the approximate centers of each grouping. However, it may be appreciated that the distance d may reflect the distance between the actual electrodes that are used to stimulate the target anatomies. For example, slight anatomical variations between patients may cause an electrode 102 near one end of group A and an electrode 102 near one end of group B to reside closest to their target anatomies. In such instances, the distance d may be measured between these electrodes. Thus, the distance d is generally measured as the distance between the target anatomies along the shaft 103 of the lead 100 and may include slight variations of endpoints within the groupings.

Figure 1C:
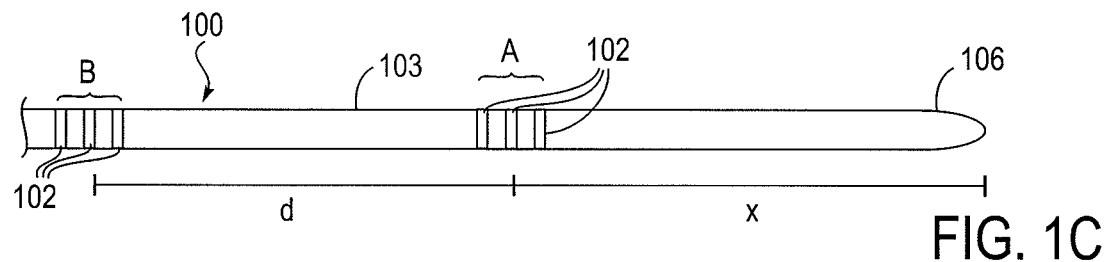

FIG. 1C illustrates an embodiment of a lead 100 having a first grouping A of electrodes 102 and second grouping B of electrodes 102, wherein the groupings are spaced apart by a distance d as described above. In addition, the lead has an elongated distal tip 106 having a length x. The elongated distal tip may be used to anchor the lead 100 in a desired position. In this embodiment, the length x is measured from the center of the first grouping A to the distal end of the distal tip 106. The length x may vary depending on the intended use of the lead 100, as will be described and illustrated in later sections. However, it may be appreciated that, in some embodiments, the length x is approximately equal to the distance d. In other embodiments, the length x is longer than the distance d. It may be appreciated that the length x may optionally be shorter than the distance d.

Figure 1D:
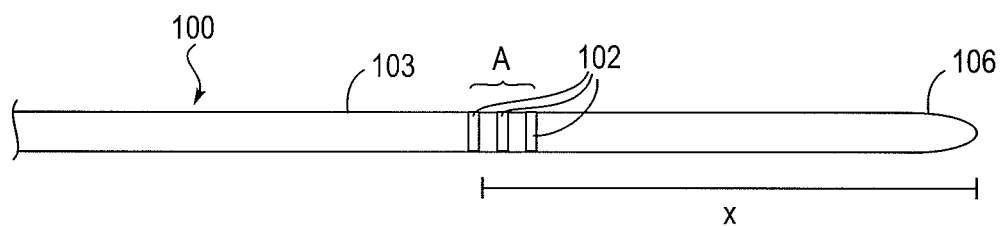

FIG. 1D illustrates an embodiment of a lead 100 having a first grouping A of electrodes 102 and an elongated distal tip 106 having a length x. Again, the length x is measured from the center of the first grouping A to the distal end of the distal tip 106. And, the length x may vary depending on the intended use of the lead 100, as will be described and illustrated in later sections.

Figure 1E:
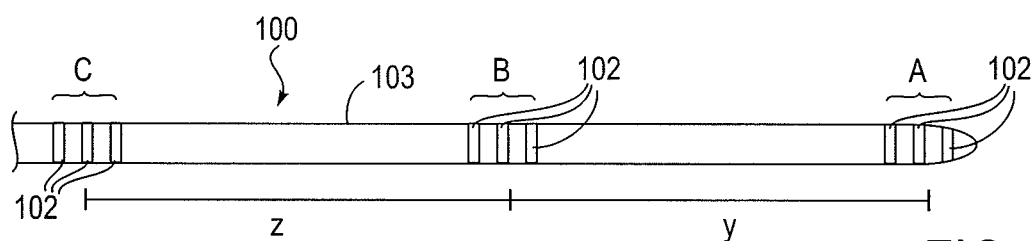

FIG. 1E illustrates an embodiment of a lead 100 having a first grouping A of electrodes 102, a second grouping B of electrodes 102 and a third grouping C of electrodes 102. The second grouping B is spaced a distance y proximally the first grouping A, and the third grouping C is spaced a distance z proximally to the second grouping B. The values for y and z may vary depending on the intended use of the lead 100, as will be described and illustrated in later sections. However, it may be appreciated that in some embodiments the distance y and/or distance z may be equal to the distance d, wherein the distance d is the distance between target anatomies, such as DRGs. It may also be appreciated that the additive value of distance y and distance z (y+z) may be equal to the distance d. For example, grouping A may reside near a target anatomy (such as a DRG1) and grouping C may reside near another target anatomy (such as DRG2), wherein the second grouping B resides therebetween to provide stimulation to a location such as a spinal cord S.

It may be appreciated that in some embodiments each electrode is individually programmed with stimulation information, such as voltage, current, pulse width, repetition rate, and burst rates. Thus, at least two of the electrodes may be programmed with different stimulation information. Likewise, in some embodiments each grouping of electrodes is individually programmed with stimulation information, such as voltage, current, pulse width, repetition rate, and burst rates. Thus, at least two of the electrode groupings may be programmed with different stimulation information. In some embodiments, the proximal end of the lead is insertable into a port in the IPG so that each electrode is provided an electrical signal via a contact within the port. However, in other embodiments wherein the number of electrodes on the lead exceeds the number of contacts within the port, the proximal end of the lead may be connected with a Y connector which splits the lead into at least two halves. Each half is insertable into the IPG so that each electrode is provided an electrical signal via a contact within the port. Any number of Y connectors can be used. Or, a multi-pronged connector can be used to achieve this end.

Figure 2A:
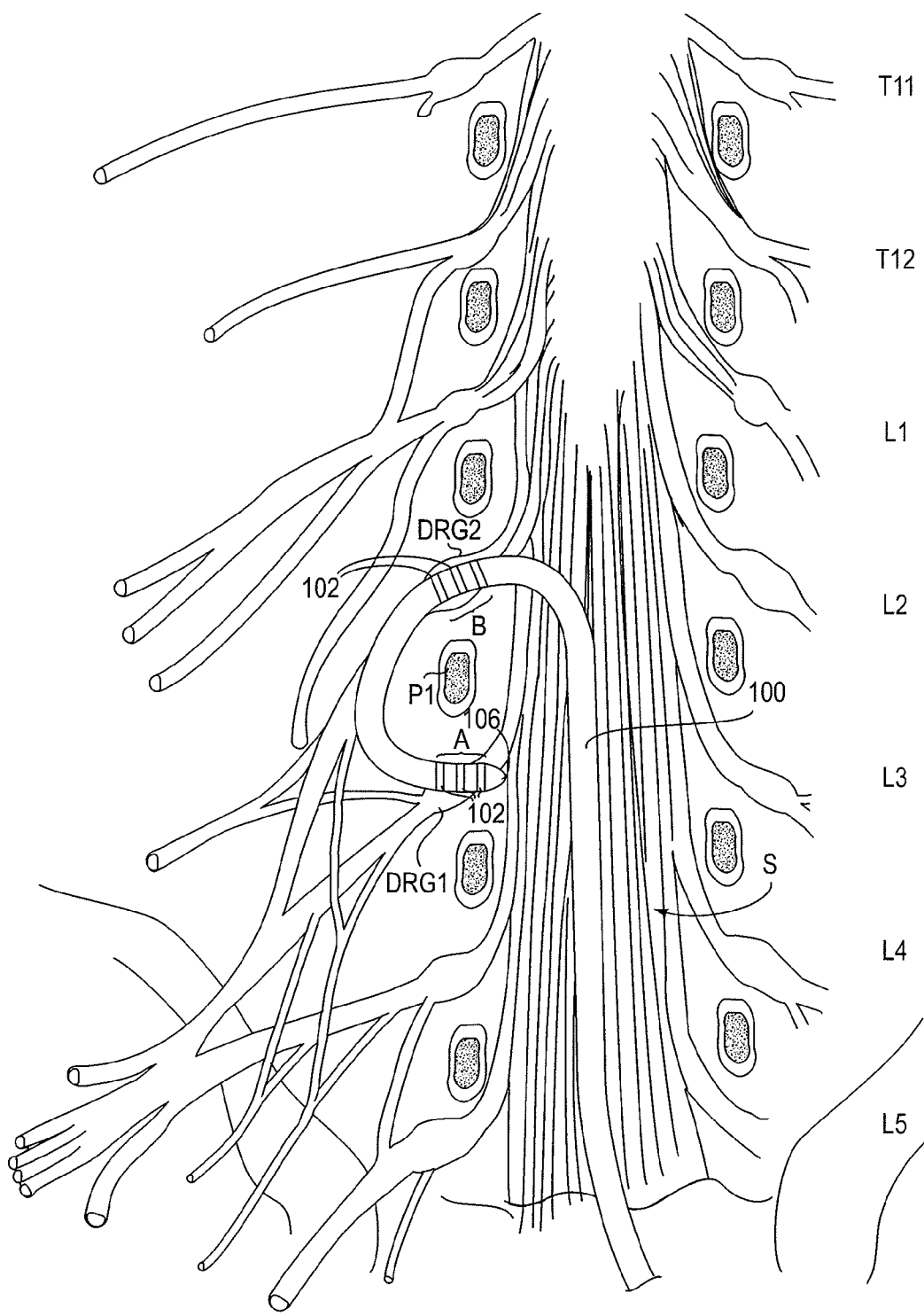
FIG. 2A illustrates an example positioning of the lead of FIG. 1A within a patient anatomy.

FIG. 2A illustrates an example positioning of the lead 100 of FIG. 1A within a patient anatomy wherein the first grouping A of electrodes 102 resides near a first target anatomy and the second grouping B of electrodes 102 resides near a second target anatomy. With respect to nomenclature, it may be appreciated that the lumbar nerve roots emerge from below the pedicle of their respective vertebrae. Thus, nerve root L2 resides below the pedicle of and at the lower half of the vertebral body of L2. Herein, the nerve roots are described as being on levels. For example, the L2 nerve roots are described to be on level L2.

In this example, the first target anatomy is a DRG1 on a first level (L3) and the second target anatomy is a DRG2 on a second level (L2), wherein a pedicle P1 resides between DRG1 and DRG2. In this embodiment, the lead 100 is advanced within the epidural space of the spinal column or spinal canal S in an antegrade approach. The lead 100 is directed laterally outward along the second level (L2) toward the DRG2 on one side of the spinal canal S. The distal tip 106 of the lead 100 is advanced through the corresponding foramen and curves down around the pedicle P1, outside of the spinal canal S. The distal tip 106 is further advanced back toward the spinal canal S, around the pedicle P1 along the first level (L3). Depending on the location of DRG1, the distal tip 106 may be advanced through the corresponding intervertebral (IV) foramen. In this embodiment, the distal tip 106 is positioned so that the first grouping A of electrodes 102 resides near DRG1 and the second grouping B of electrodes 102 resides near DRG2. Thus, the distance d is equal to at least the anatomical distance of half of the diameter of the intervertebral foramen corresponding to DRG1, half of the circumference of pedicle P1 and half of the diameter of the intervertebral foramen corresponding to DRG2. This may be calculated as the average diameter of an intervertebral foraminal opening (approximately 13-22 mm, typically approximately 18 mm) plus the average pedicle height (approximately 13-24 mm, typically approximately 18 mm) plus the average pedicle width (approximately 6-18 mm, typically approximately 12 mm). Thus, in some instances, the distance d is in the range of at least approximately 45-50 mm, particularly at least approximately 48 mm. Anatomical differences, such as due to degeneration, injury, gender and natural variation, may reduce distance d to the range of at least approximately 30-35 mm, particularly at least approximately 32 mm, or may increase the distance d to the range of at least approximately 60-65 mm, particularly at least approximately 64 mm. Therefore, in some embodiments, the distance d ranges from at least approximately 30-65 mm. It may also be appreciated that in some embodiments, the distance d is greater than the anatomical distances calculated above, wherein any excess length simply resides within the anatomy (such as extending laterally outwardly) while the groupings of electrodes reside near their respective DRGs. Thus, distance d may optionally be greater than 65 mm.

In FIG. 2A, the lead 100 is illustrated such that the electrode groupings A, B are disposed on the respective DRGs, however it may be appreciated that the groupings A, B may reside at various locations near or in the vicinity of the respective DRGs. Likewise, the lead 100 may be positioned against the pedicle P1 at one or more locations. The lead 100 may also be positioned against other pedicles or other anatomies, such as to assist in curving the lead 100 around pedicle P1.

Positioning of the lead 100 as in FIG. 2A allows for treatment of multiple targeted anatomies, DRG1 and DRG2, with a single device. Thus, DRGs on two separate levels can be stimulated with a single lead rather than two separate leads. This reduces possible complications related to the placement of multiple devices. DRG1 and DRG2 can be simultaneously stimulated or stimulated separately at desired intervals. In addition, such positioning provides improved anchoring. For example, the curvature of the lead 100 around the pedicle P1 resists migration or pull-out of the lead 100 due to movement of the patient. However, the lead 100 can be withdrawn for removal or repositioning of the lead 100.

It may be appreciated that the embodiment of the lead 100 of FIG. 1C may be similarly positioned wherein the first grouping A of electrodes 102 resides near DRG1 and the second grouping B of electrodes 102 resides near DRG2. The elongated distal tip would extend further, such as into the spinal canal S, for additional anchoring. Thus, the distance d is equal to at least the anatomical distance of half of the diameter of the intervertebral foramen corresponding to DRG1, half of the circumference of pedicle P1 and half of the diameter of the intervertebral foramen corresponding to DRG2, as described above. In addition, length x of the elongated distal tip 106 is sufficiently long to provide desired anchoring. In some embodiments, length x is equal to ½ of a vertebral segment height or spinal level. In some instances, the vertebral segment height or spinal level is calculated as the sum of the height of a pedicle and the diameter of an intervertebral foraminal opening. An average pedicle height of approximately 18 mm and an average intervertebral foraminal opening of approximately 18 mm would provide a vertebral segment height of 36 mm and a length x of approximately 18 mm. In smaller anatomies, the pedicle height of approximately 13 mm and the intervertebral foraminal opening of approximately 13 mm would provide a vertebral segment height of 26 mm and a length x of approximately 13 mm. In larger anatomies, the pedicle height of approximately 23 mm and the intervertebral foraminal opening of approximately 23 mm would provide a vertebral segment height of 46 mm and a length x of approximately 23 mm. It may be appreciated that in some embodiments the length x is equal to one, two, three, four, five, six or more vertebral segment heights or spinal levels. Thus, the length x may average approximately 36 mm, 72 mm, 108 mm, 144 mm, 180 mm, 216 mm or more. It may be appreciated that the length x may alternatively be more or less than incremental vertebral segment heights or spinal levels.

Figure 2B:
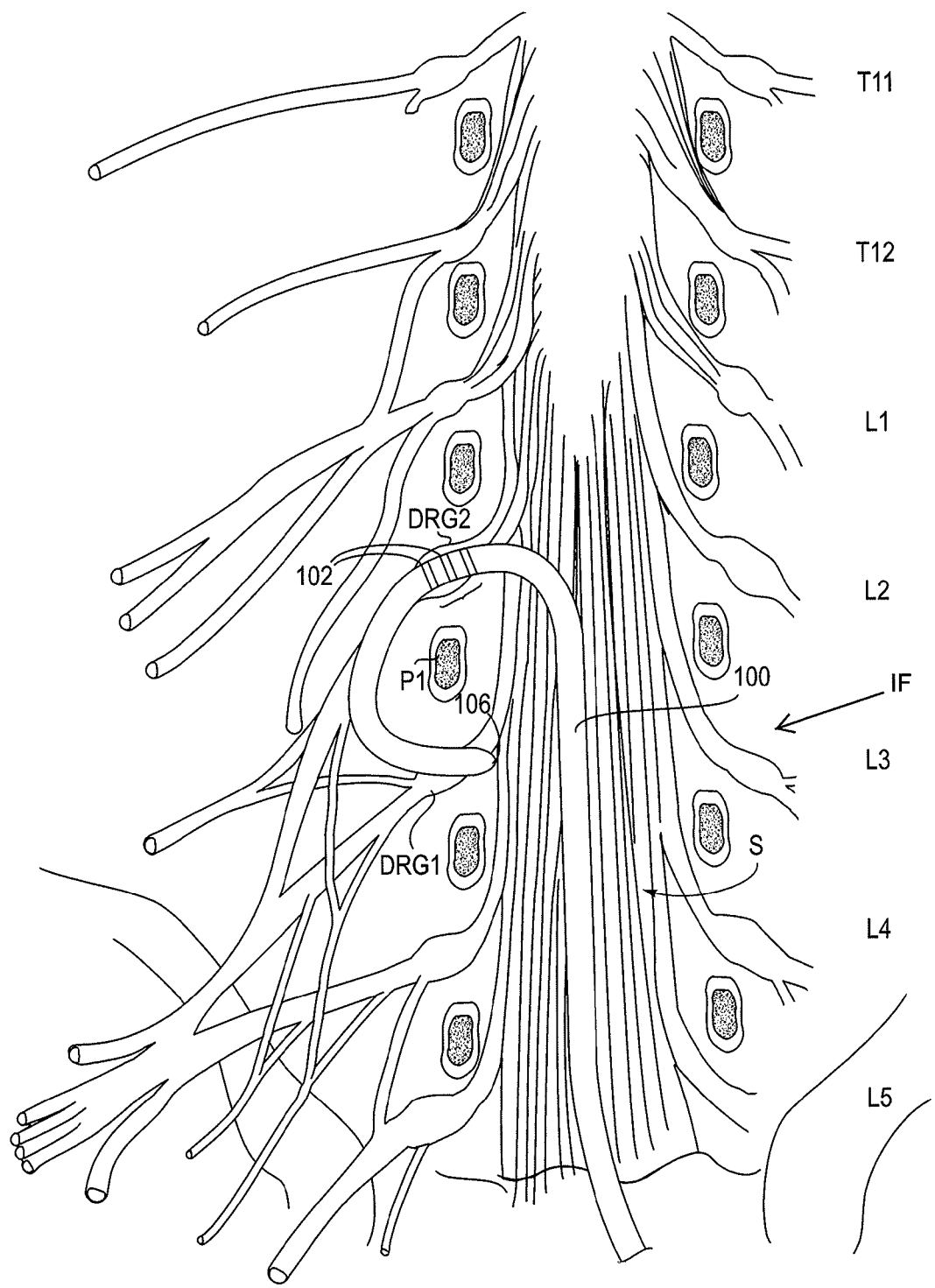
FIG. 2B illustrates an example positioning of another embodiment of a lead of the present invention within a patient anatomy.

FIG. 2B illustrates the embodiment of the lead 100 of FIG. 1D in a similar positioning. Here, the first grouping A is positioned near DRG2 and the elongated distal tip 106 extends around the pedicle P1 along the first level (L3), as described above, and is used to anchor the lead 100 in position. Thus, the length x is approximately equal to the distance d. For example, the length x may be equal to at least the anatomical distance of half of the diameter of the intervertebral foramen corresponding to DRG 1, half of the circumference of pedicle P1 and half of the diameter of the intervertebral foramen corresponding to DRG2, as described in relation to distance d above. It may be appreciated that in some embodiments, the distal tip 106 extends further, such as into the spinal canal S, for additional anchoring. In such embodiments, the length x is longer than the distance d. In some embodiments, the length x is longer than distance d by ½, one, two, three, four, five, six or more vertebral segment heights or spinal levels.

It may be appreciated that the lead 100 may be positioned in a similar manner with a retrograde approach. In such an approach, the lead 100 is directed laterally outward toward the DRG1 on one side of the spinal canal S. The distal tip 106 of the lead 100 is advanced and curves up around the pedicle P1, outside of the spinal canal S. The distal tip 106 is further advanced back toward the spinal canal S, around the pedicle P1 toward DRG2. It may also be appreciated that the lead 100 may be positioned by entering the spinal canal with a contralateral or ipsilateral approach. Such entrance points may be on the same level as one of the target DRGs.

Figure 3:
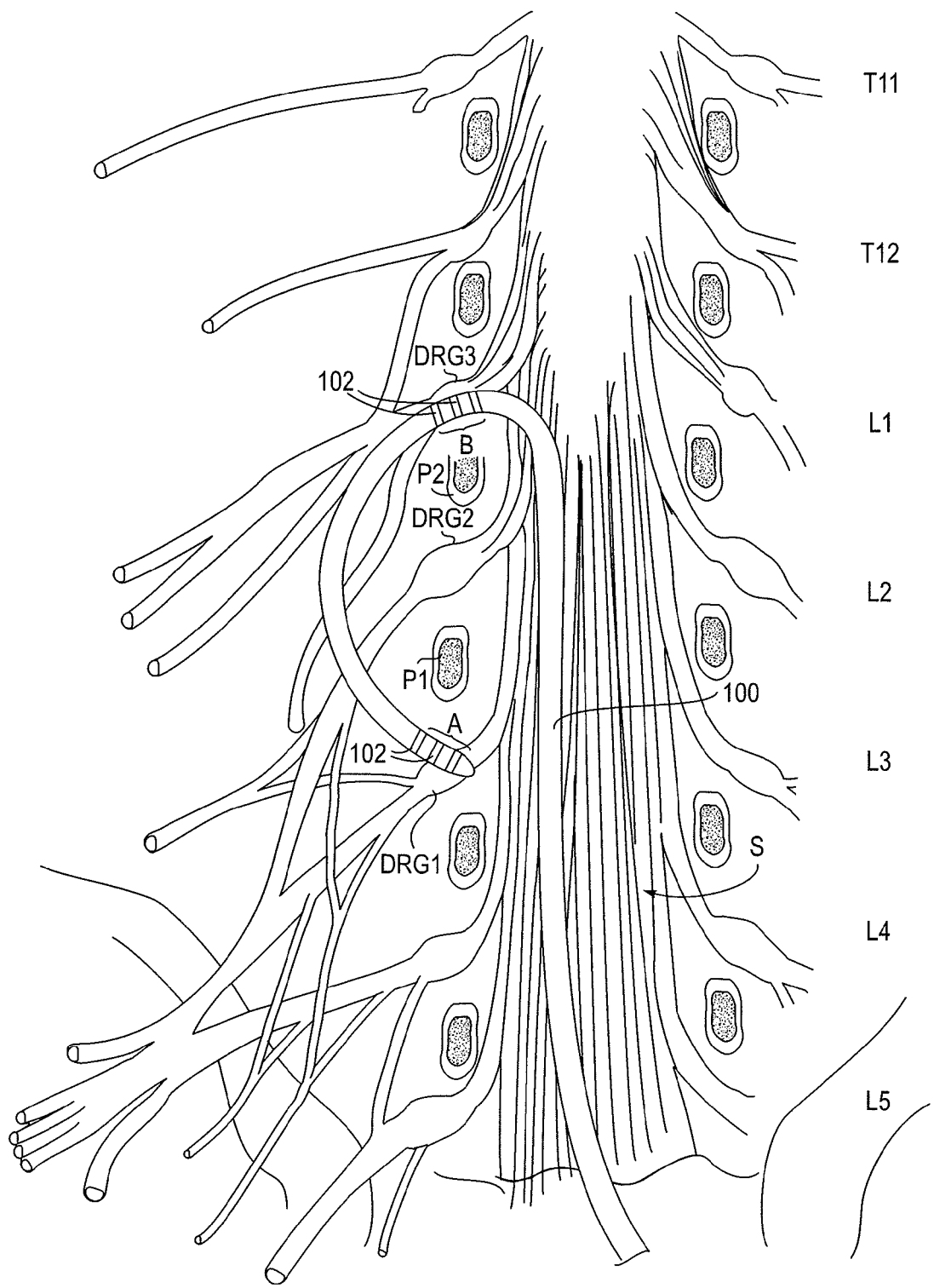
FIG. 3 illustrates another example positioning of the lead of FIG. 1A within a patient anatomy.

FIG. 3 illustrates another example positioning of the lead 100 of FIG. 1 A within a patient anatomy wherein the first grouping A of electrodes 102 resides near a first target anatomy and the second grouping B of electrodes 102 resides near a second target anatomy. In this example, the first target anatomy is a DRG1 on a first level (L3) and the second target anatomy is a DRG3 on a third level (L1), wherein pedicle P1, DRG2 and pedicle P2 resides between DRG1 and DRG3. Thus, the DRGs are stimulated on levels that are not adjacent to each other, and DRG2 on the second level (L2) is not directly stimulated. In some instances, skipping one or more levels is desirable when ascending and descending pain pathways between spinal levels allow therapeutic benefit to a spinal level which is not directly stimulated. This technique maximizes the coverage area and minimizes the number of needle sticks and potentially the number of complications. In this embodiment, the lead 100 is advanced within the epidural space of the spinal canal S in an antegrade approach. The lead 100 is directed laterally outward along the third level (L1) toward the DRG3 on one side of the spinal canal S. The distal tip 106 of the lead 100 is advanced through the corresponding intervertebral foramen and curves down around the pedicle P2, outside of the spinal canal S. The distal tip 106 is further advanced in a retrograde manner outside of the spinal canal S, bypassing DRG2. The distal tip 106 is further advanced back toward the spinal canal S, around the pedicle P1 and toward DRG1 along the first level (L3). Depending on the location of DRG1, the distal tip 106 may also pass through the corresponding intervertebral foramen. In this embodiment, the distal tip 106 is positioned so that the first grouping A of electrodes 102 resides near DRG1 and the second grouping B of electrodes 102 resides near DRG3.

In this embodiment, the distance d is equal to at least the anatomical distance of half of the diameter of the intervertebral foramen corresponding to DRG1, half of the circumference of pedicle P1, the diameter of the intervertebral foramen corresponding to DRG2, half the circumference of pedicle P2, and half of the diameter of the intervertebral foramen corresponding to DRG3. This may be calculated as twice the average diameter of an intervertebral foraminal opening (approximately 26-44 mm, typically approximately 36 mm) plus twice the average pedicle height (approximately 26-48 mm, typically approximately 36 mm) plus the average pedicle width (approximately 6-18 mm, typically approximately 12 mm). Thus, in some instances, the distance d is in the range of approximately 80-90 mm, particularly approximately 84 mm. Anatomical differences, such as due to degeneration, injury, gender and natural variation, may reduce distance d to the range of approximately 50-65 mm, particularly approximately 58 mm, or may increase the distance d to the range of approximately 100-120 mm, particularly approximately 110 mm. Therefore, in some embodiments, the distance d ranges from approximately 50-110 mm.

In FIG. 3, the lead 100 is illustrated such that the electrode groupings A, B are disposed on the respective DRGs, however it may be appreciated that the groupings A, B may reside at various locations near or in the vicinity of the respective DRGs. Likewise, the lead 100 may be positioned against the pedicles P1, P2 at one or more locations. The lead 100 may also be positioned against other pedicles or other anatomies, such as to assist in curving the lead 100 around the pedicles P1, P2.

It may be appreciated that the lead 100 embodiments of FIG. 1C and FIG. 1D may be similarly positioned. It may also be appreciated that the lead 100 may be positioned so as to stimulate DRGs on non-adjacent levels in a similar manner with a retrograde approach. In such an approach, the lead 100 is directed laterally outward along the third level (L3) toward the DRG1 on one side of the spinal canal S. The distal tip 106 of the lead 100 is advanced beyond curves up around the pedicle P1, outside of the spinal canal S. The distal tip 106 is further advanced in an antegrade manner outside of the spinal canal S, bypassing DRG2. The distal tip 106 is further advanced back toward the spinal canal S, around the pedicle P2 and along the first level (L1).

Figure 4:
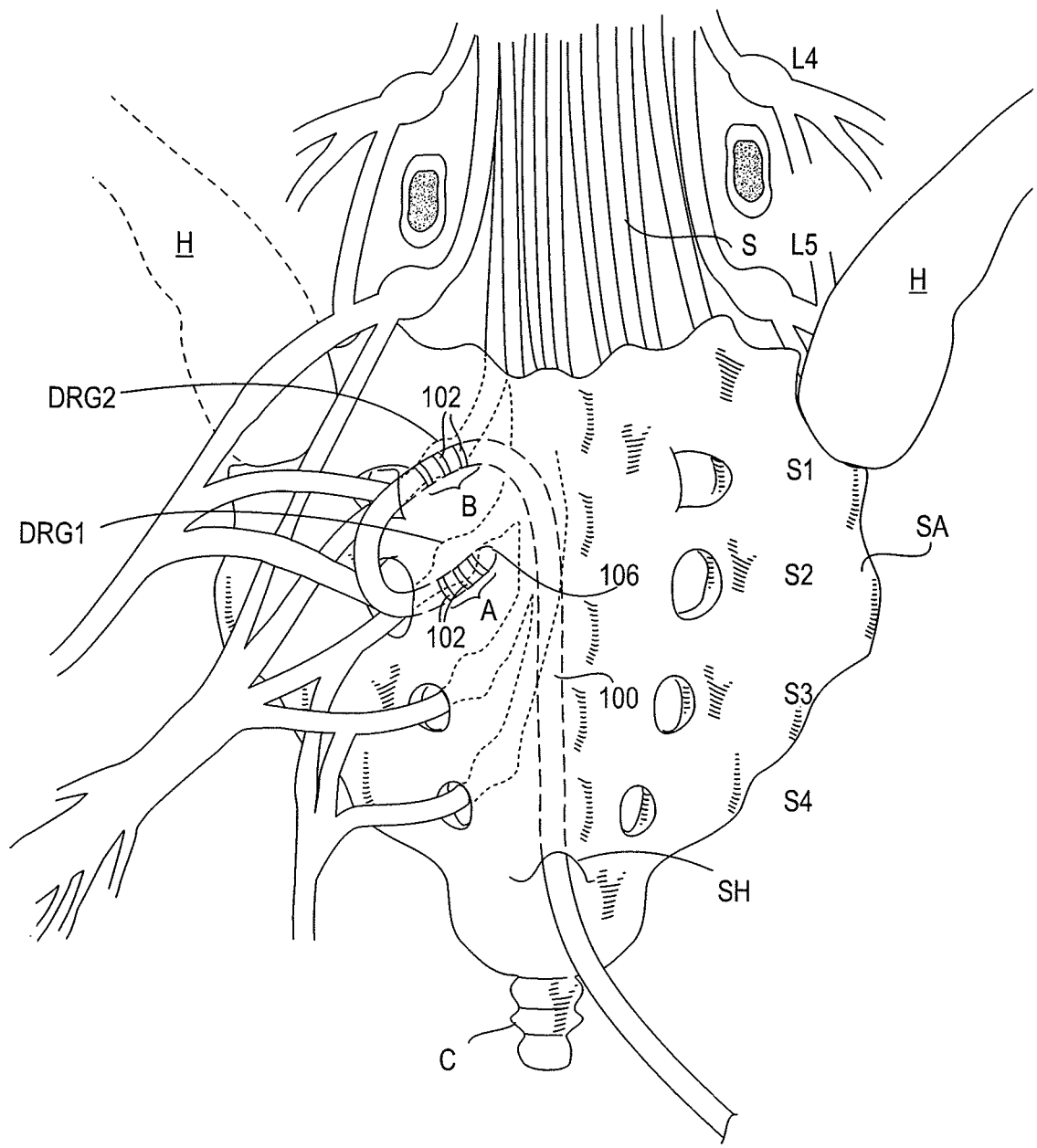
FIG. 4 illustrates an example positioning of a lead within a sacrum of a patient.

FIG. 4 illustrates an example positioning of the lead 100 within a sacrum SA of a patient. The sacrum SA is a large, triangular bone near the base of the spinal canal S, where it is inserted like a wedge between the two pelvic or hip bones H. Its upper part connects with the last lumbar vertebra L5, and bottom part with the coccyx C. The DRGs in the sacral region are disposed on dorsal roots which extend laterally outwardly at a steeper angle and may be found in a different location than the DRGs in the cervical, thoracic and lumbar regions. For example, unlike the lumbar region where over 90% of DRGs lie within an intraforaminal space, the DRGs in the sacral region are located either inside the spinal canal or intraforaminally. For the S1 DRG, approximately 55-60% are located in the foramen and 40-45% are located in the canal. For the S2 DRG, it is varied with more DRGs located inside the canal. And, typically, all S3 and S4 DRGs are located within the canal. FIG. 4 illustrates an anatomy wherein each of the DRGs (at levels S1, S2, S3, S4) is located within the canal.

In this example, the lead 100 is advanced through the sacral hiatus SH, the opening into the vertebral canal in the midline of the dorsal surface of the sacrum between the laminae of the fifth sacral vertebra, in an antegrade direction. Again, the lead 100 is positioned so that the first grouping A of electrodes 102 resides near a first target anatomy and the second grouping B of electrodes 102 resides near a second target anatomy. Here, the first target anatomy is a DRG1 on a first level (S2) and the second target anatomy is a DRG2 on a second level (S2). The lead 100 is advanced within the epidural space of the spinal canal S and is directed laterally outward along the second level (S1) toward the DRG2 on one side of the spinal canal S. The distal tip 106 of the lead 100 is advanced beyond the DRG2 (through the corresponding foramen) and curves down along the sacrum SA, outside of the sacrum SA. The distal tip 106 is further advanced back toward the spinal canal S and into an adjacent foramen leading to DRG 1 along the first level (S2). In this embodiment, the distal tip 106 is positioned so that the first grouping A of electrodes 102 resides near DRG1 and the second grouping B of electrodes 102 resides near DRG2.

Thus, in this embodiment, the distance d is equal to at least the anatomical distance of between the sacral foramen. In some instances, the distance d is in the range of approximately 30-35 mm, particularly approximately 32 mm. Anatomical differences, such as due to degeneration, injury, gender and natural variation, may reduce distance d to the range of approximately 22-28 mm, particularly approximately 25 mm, or may increase the distance d to the range of approximately 38-50 mm, particularly approximately 42 mm. Therefore, in some embodiments, the distance d ranges from approximately 22-50 mm.

In FIG. 4, the lead 100 is illustrated such that the electrode groupings A, B are disposed on the respective DRGs, however it may be appreciated that the groupings A, B may reside at various locations near or in the vicinity of the respective DRGs.

Positioning of the lead 100 as in FIG. 4 has some particular advantages to stimulating the sacral region. Stimulation of the sacral region is used to treat pain but also to treat a variety of other pelvic floor disorders. Pelvic floor disorders include urinary incontinence, constipation, rectal pain, vaginal and/or rectal prolapse, pelvic pain/trauma, and sexual dysfunction (Dyspareunia, Apareunia). Previous surgical methods to implant a neurostimulation lead in a patient's sacrum to treat pelvic floor disorders have been invasive by requiring a large sacral incision in a procedure known as dissection. Dissection involves making a midline incision over the sacrum from below S4 up to S1. After the incision is made, the paraspinal muscle fibers are split and sharply retracted. The sacral foramen are then exposed. Once the desired foramen is located, another small incision is made over the desired foramen that is large enough to allow insertion of the stimulation lead. The stimulation lead is inserted through the incision. Surgically implanting the stimulation lead in this manner can cause patient complications, create significant patient recovery time and create a significant expense to the healthcare system. In addition, anchoring of the lead is typically achieved by suturing to tissue surrounding the sacrum. That tissue, however, is relatively weak and only one or two sutures may be placed through it. Even then the fixation of the lead is less than wholly reliable. In addition, while the lead is being sutured to the tissue, the lead may move from the optimal site. Movement of the lead, whether over time from suture release or during implantation, has undesired effects. For example, unintended movement of an object positioned proximate a nerve may cause unintended nerve damage. Moreover reliable stimulation of a nerve requires consistent nerve response to the electrical stimulation which, in turn, requires consistent presence of the electrode portion of the lead proximate the nerve. In some instances, more reliable anchoring has been attempted by attaching the lead to the sacrum itself with the use of bone screws. Among other complications, such anchoring is typically invasive, difficult to achieve and even more difficult to reverse for removal of the lead.

Positioning of the lead 100 of the present invention in a manner such as illustrated in FIG. 4 is minimally invasive and provides ease of placement, anchoring and removal. The curvature of the lead 100 through one foramen and into another foramen resists migration or pull-out of the lead 100. However, the lead 100 can be easily withdrawn for removal or repositioning of the lead 100 since it is not sutured or screwed in place.

It may be appreciated that the lead 100 may be positioned within the sacrum SA in a manner similar to FIG. 4 wherein DRGs are stimulated on levels that are not adjacent to each other. In an example of such an embodiment, the lead 100 is advanced within the epidural space of the spinal canal S and is directed laterally outward along the second level (S1) toward the DRG2 on one side of the spinal canal S. The distal tip 106 of the lead 100 is advanced beyond the DRG2 (through the corresponding foramen) and curves down along the sacrum SA, outside of the spinal canal S. The distal tip 106 is further advanced back toward the spinal canal S and into a non-adjacent foramen leading to DRG1 along the first level (S3). Thus, the DRG at level S2 is skipped over and not stimulated. Skipping one or more levels may be desirable due to ascending and descending pain pathways between spinal levels which may allow therapeutic benefit to a spinal level which is not directly stimulated. In such embodiments, the distance d is at least the distance between the foramen that are entered. For example, when one level is skipped, the distance d is equal to at least twice the average anatomical distance between sacral foramen. In some instances, the distance d is in the range of approximately 60-70 mm, particularly approximately 64 mm. When two levels are skipped, the distance d is equal to at least three times the average anatomical distance between sacral foramen. In some instances, the distance d is in the range of approximately 80-100 mm, particularly approximately 96 mm. In some instances the DRGs are stimulated in both the sacrum and above the sacrum. For example, the lead 100 may be positioned so that the first grouping A of electrodes 102 resides near a DRG on level S1 and the second grouping B of electrodes 102 resides near a DRG on level L5. In such instances, the distance d is at least the distance between the associated foramen.

Further, it may be appreciated that the lead 100 may be positioned within the sacrum SA so as to stimulate DRGs on adjacent or non-adjacent levels in a similar manner with a retrograde approach. In such an approach, the lead 100 is inserted above the sacrum SA and advanced downward into the sacral region. In one embodiment the lead 100 is advanced within the epidural space of the spinal canal S and is directed laterally outward toward DRG1 on one side of the spinal canal S. The distal tip 106 of the lead 100 is advanced beyond the DRG1 (through the corresponding foramen) and curves up along the sacrum SA, outside of the sacrum SA. The distal tip 106 is further advanced back toward the spinal canal S and into an adjacent foramen leading to DRG2.

Likewise, it may be appreciated that the lead 100 embodiments of FIG. 1C and FIG. 1D may be similarly positioned (antegrade, retrograde, adjacent levels, non-adjacent levels, etc. In some embodiments, the distal tip 106 extends further into the sacrum SA or up into the spinal canal S for additional anchoring. In such embodiments, the length x of the elongated distal tip 106 is in the range of approximately ½, one, two, three, four, five, six or more vertebral segment heights or spinal levels.

Figure 5A:
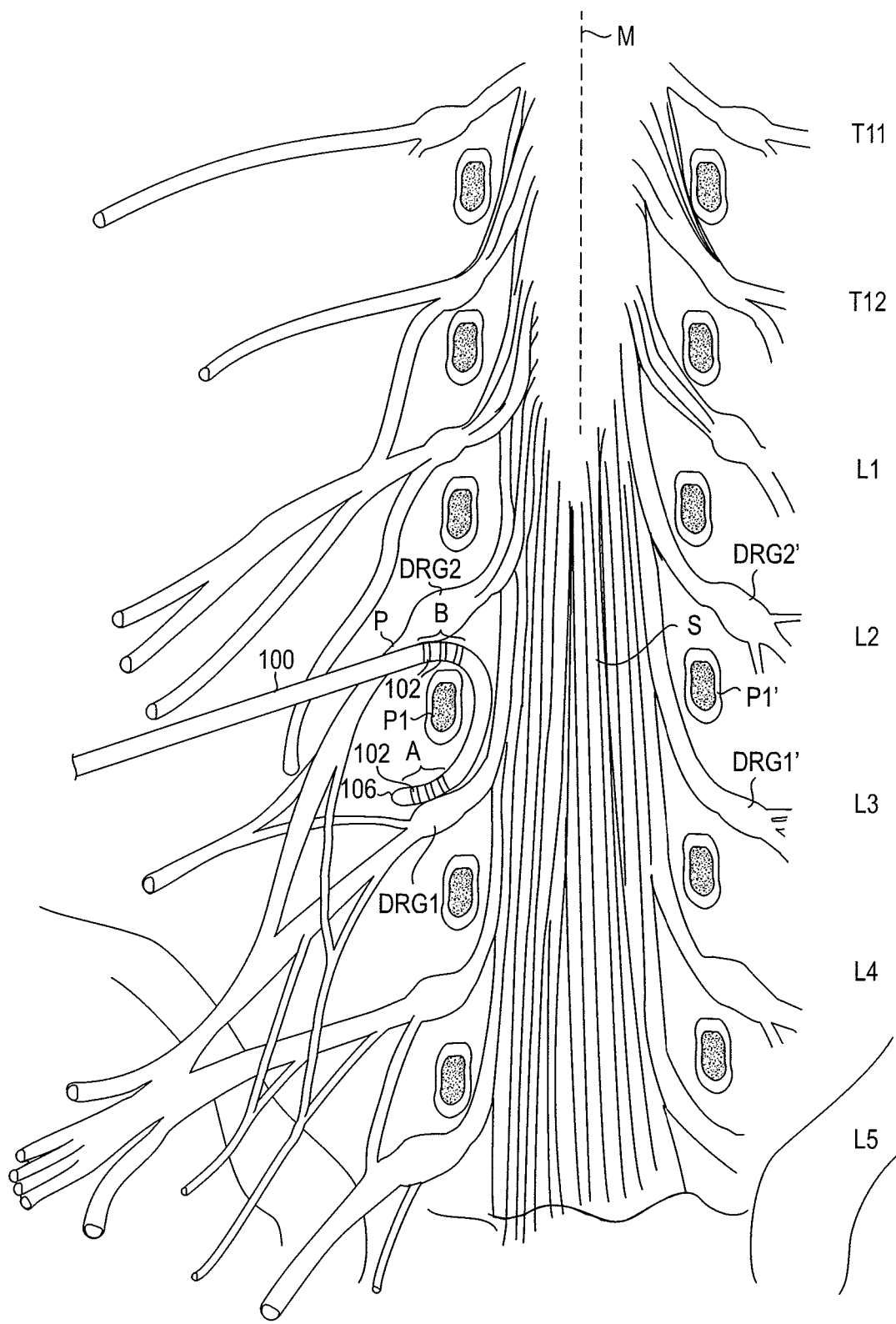
FIG. 5A illustrates an example positioning of a lead within a patient anatomy wherein the lead is advanced extraforaminally.

FIG. 5A illustrates another example positioning of the lead 100 of the present invention within a patient anatomy wherein the first grouping A of electrodes 102 resides near a first target anatomy and the second grouping B of electrodes 102 resides near a second target anatomy. In this example, the first target anatomy is a DRG 1 on a first level (L3) and the second target anatomy is a DRG2 on a second level (L2), wherein a pedicle P1 resides between DRG1 and DRG2. In this embodiment, the lead 100 is advanced extraforaminally, or from an "outside-in" approach, such as along a peripheral nerve P, transverse process or other bony structure, toward a DRG and a spinal canal S. To begin, the distal tip 106 of the lead 100 is advanced toward DRG2 and through the corresponding intervertebral foramen along the second level (L2) and curves down around the pedicle P1 along the spinal canal S, within the epidural space. The distal tip 106 is further advanced away from the spinal canal S, toward DRG1 along the first level (L3) (and may pass through the corresponding intervertebral foramen depending on the location of DRG1). In this embodiment, the distal tip 106 is positioned so that the first grouping A of electrodes 102 resides near DRG1 and the second grouping B of electrodes 102 resides near DRG2.

In such embodiments, the distance d is equal to at least the anatomical distance of half of the diameter of the intervertebral foramen corresponding to DRG1, half of the circumference of pedicle P1 and half of the diameter of the intervertebral foramen corresponding to DRG2. This may be calculated as the average diameter of an intervertebral foraminal opening (approximately 13-22 mm, typically approximately 18 mm) plus the average pedicle height (approximately 13-24 mm, typically approximately 18 mm) plus the average pedicle width (approximately 6-18 mm, typically approximately 12 mm). Thus, in some instances, the distance d is in the range of approximately 45-50 mm, particularly approximately 48 mm. Anatomical differences, such as due to degeneration, injury, gender and natural variation, may reduce distance d to the range of approximately 30-35 mm, particularly approximately 32 mm, or may increase the distance d to the range of approximately 60-65 mm, particularly approximately 64 mm. Therefore, in some embodiments, the distance d ranges from approximately 30-65 mm.

In FIG. 5A, the lead 100 is illustrated such that the electrode groupings A, B are disposed near the respective DRGs, however it may be appreciated that the groupings A, B may reside at various locations on or in the vicinity of the respective DRGs. Likewise, the lead 100 may be positioned against the pedicle P1 at one or more locations. The lead 100 may also be positioned against other pedicles or other anatomies, such as to assist in curving the lead 100 around the pedicles P1.

It may be appreciated that the distal tip 106 may be advanced further down the spinal canal S and then advanced away from the spinal canal S toward a non-adjacent DRG so as to stimulate multiple non-adjacent levels. Likewise, the lead 100 may be positioned so as to curve up through the spinal canal S and advance away from the spinal canal along an adjacent or non-adjacent level thereabove. Still further, it may be appreciated that the lead 100 may pass through the epidural space and across the midline M of the spinal canal S to wrap around a pedicle P1' on the opposite side. In such an embodiment, the lead 100 is advanced extraforaminally, or from an "outside-in" approach, such as along a peripheral nerve P, transverse process or other bony structure, toward DRG2 and the spinal canal S. The distal tip 106 of the lead 100 is advanced toward DRG2 and through the corresponding intervertebral foramen along the second level (L2) and crosses the midline M of the spinal canal S. The distal tip 106 then advances toward DRG2' and passes through the associated intervertebral foramen. The distal tip 106 then curves down around the pedicle P1' and toward DRG1' along the first level (L3) (and may pass through the corresponding intervertebral foramen depending on the location of DRG1'). In this embodiment, the distal tip 106 is positioned so that the first grouping A of electrodes 102 resides near DRG1' and the second grouping B of electrodes 102 resides near DRG2'.

Figure 5B:
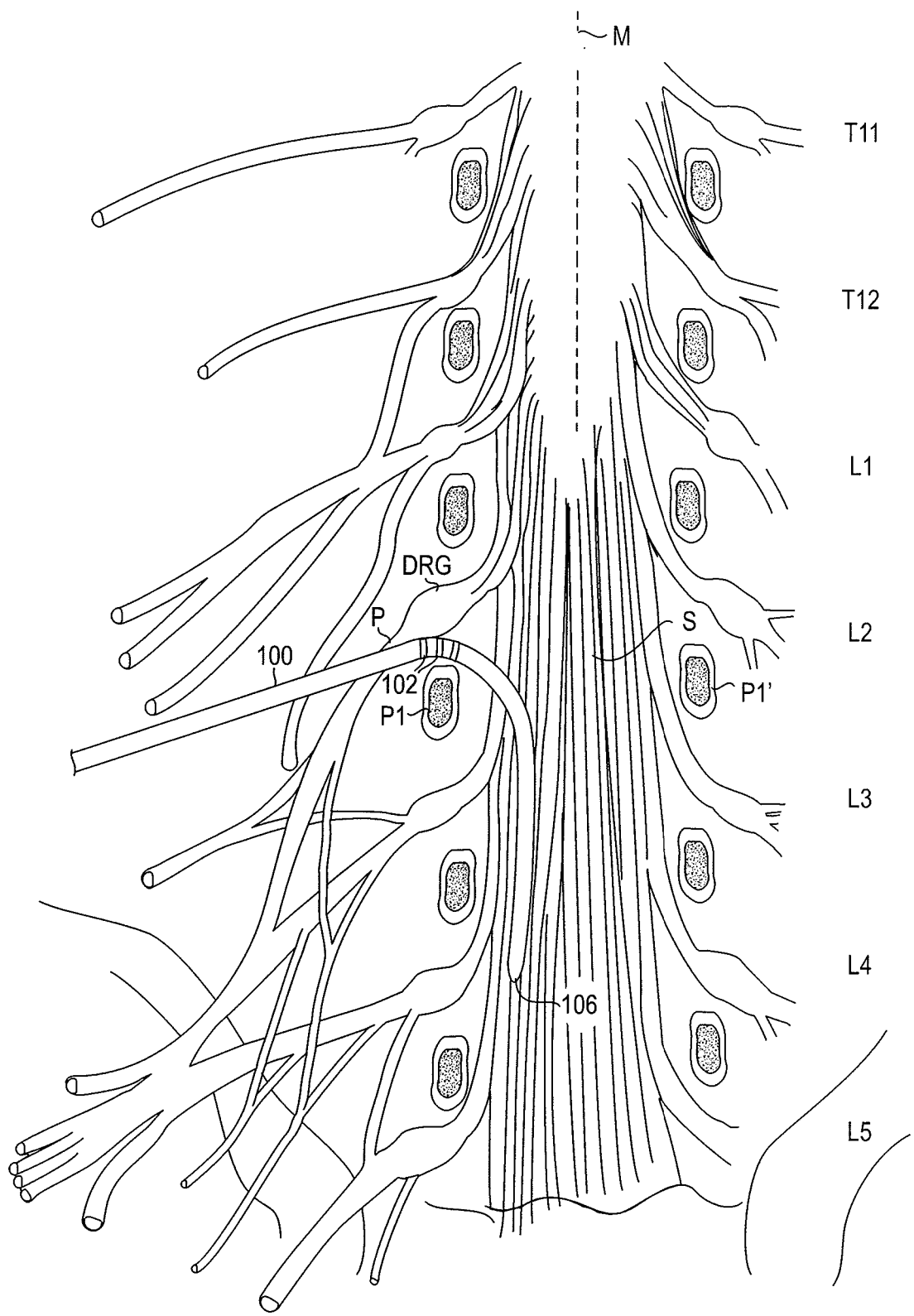
FIG. 5B illustrates an example positioning of a lead having an elongated distal tip within a patient anatomy wherein the elongated distal tip is positioned within the spinal canal.

Referring to FIG. 5B, a lead 100 embodiment as in FIG. 1D is shown similarly positioned. Here, the grouping A of electrodes 102 resides near a target anatomy (DRG) and the elongated distal tip 106 extends into the spinal canal S. In this example the distal tip 106 extends in a retrograde direction, however it may be appreciated that the distal tip 106 may extend in an antegrade direction. In either instance, the distal tip 106 extends sufficient distance to provide anchoring. Thus, in various embodiments, the length x is approximately equal to the distance of one half of a spinal level (approximately 26 mm), one spinal level (approximately 48 mm), two spinal levels (approximately 58 mm), three spinal levels (approximately 78 mm), four spinal levels (approximately 104 mm), or more. It may also be appreciated that the elongated distal tip 106 may cross the midline M of the spinal canal S and pass partially through an intervertebral foramen or wrap around a pedicle P1' on the opposite side.

It may also be appreciated that the methods and devices of FIG. 5A and FIG. 5B may also be applied to the sacrum SA. Thus, the lead 100 is advanced extraforaminally, or from an "outside-in" approach, toward a DRG and a spinal canal S. To begin, the distal tip 106 of the lead 100 is advanced toward DRG2 and through the corresponding foramen along the second level (S1). The distal tip 106 curves down around within the sacrum SA toward the DRG1 along the first level (S2) and may optionally pass through the corresponding foramen. When using a lead 100 embodiment as in FIG. 5B, the elongated distal tip 106 may extends and reside within the sacrum S for anchoring. Or, the elongated distal tip 106 may curve around within the sacrum towards or within another foramen.

The lead 100 may be positioned in the above arrangements with a variety of delivery systems. FIGS. 6A-6D illustrate one embodiment of a lead 100 (FIG. 6A) and compatible delivery system 120 including a sheath 122 (FIG. 6B), stylet 124 (FIG. 6C) and introducing needle 126 (FIG. 6D). As shown, the lead 100 comprises a shaft 103 having three electrodes 102 disposed near the distal tip 106 (forming a first grouping A) and three electrodes 102 disposed along the shaft 103 at least a distance d from the distal tip 106 (forming a second grouping B). In this embodiment, the lead 100 has a closed-end distal tip 106. The distal tip 106 may have a variety of shapes including a rounded shape, such as a ball shape (shown) or tear drop shape, and a cone shape, to name a few. These shapes provide an atraumatic tip for the lead 100 as well as serving other purposes. The lead 100 also includes a stylet lumen 104 which extends toward the closed-end distal tip 106.

Figure 7:
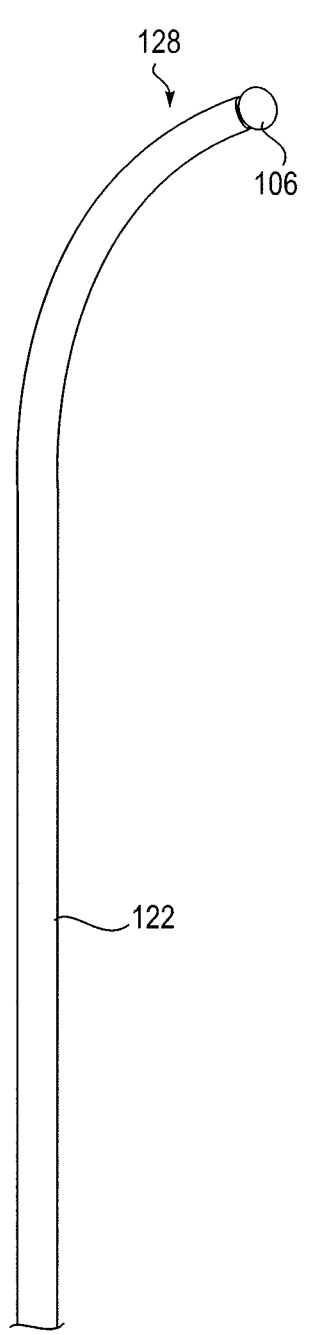
FIG. 7 illustrates an embodiment of a sheath advanced over the shaft of the lead until a portion of its distal end abuts the distal tip of the lead.

FIG. 6B illustrates an embodiment of a sheath 122 of the present invention. The sheath 122 has a distal end 128 which is pre-curved to have an angle α, wherein the angle α is in the range of approximately 80 to 165 degrees. The sheath 122 is sized and configured to be advanced over the shaft 103 of the lead 100 until a portion of its distal end 128 abuts the distal tip 106 of the lead 100, as illustrated in FIG. 7. Thus, the ball shaped tip 106 of this embodiment also prevents the sheath 122 from extending thereover. Passage of the sheath 122 over the lead 100 causes the lead 100 to bend in accordance with the precurvature of the sheath 122. Thus, when positioning the lead 100 such as in FIGS. 2-3, the sheath 122 assists in steering the lead 100 along the spinal canal S and toward a target DRG, such as in a lateral direction. Similarly, when positioning the lead 100 such as in FIG. 4, the sheath 122 assists in steering the lead 100 through the sacrum SA and toward a target DRG, such as in a lateral direction. When positioning the lead 100 such as in FIG. 5, the sheath 122 assists in steering the lead 100 along the peripheral nerves P and toward the spinal canal S, around the pedicle P1.

Figure 8:
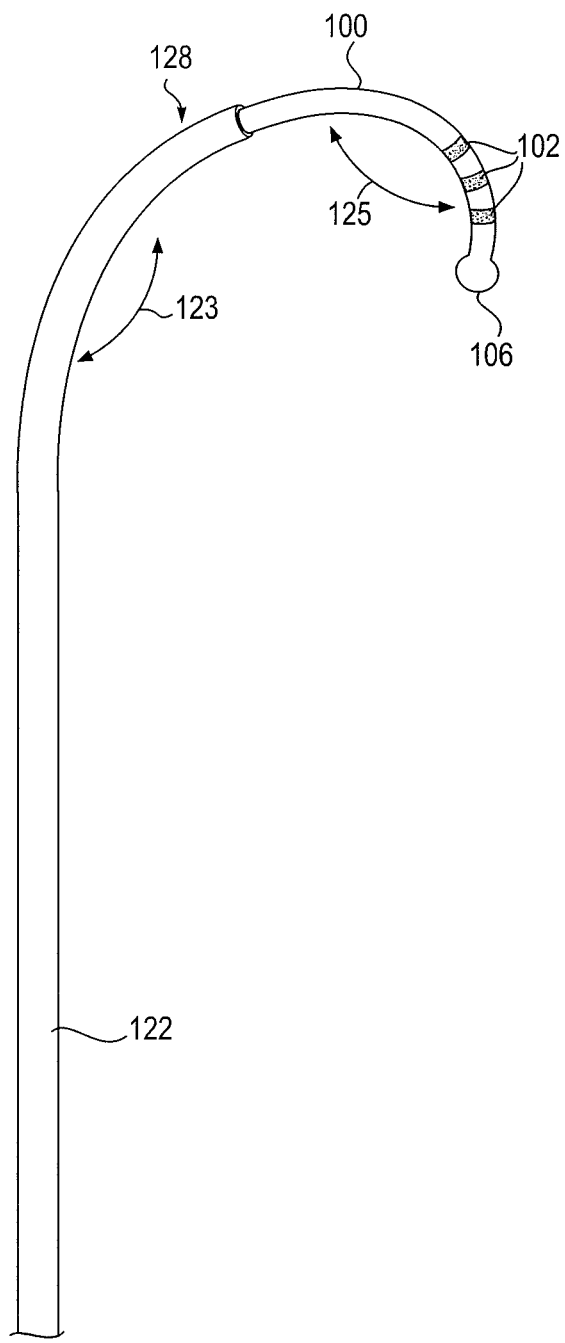
FIG. 8 illustrates an embodiment of a stylet disposed within the lead, wherein extension of the lead and stylet through the sheath bends or directs the lead through a first curvature and extension of the lead and stylet beyond the distal end of the sheath allows the lead to bend further along a second curvature.

Referring back to FIG. 6C, an embodiment of a stylet 124 of the present invention is illustrated. The stylet 124 has a distal end 130 which is pre-curved so that its radius of curvature is in the range of approximately 0.1 to 0.5 inches. The stylet 124 is sized and configured to be advanced within the stylet lumen 104 of the lead 100. Typically the stylet 124 extends therethrough so that its distal end 130 aligns with the distal end 101 of the lead 100. Passage of the stylet 124 through the lead 100 causes the lead 100 to bend in accordance with the precurvature of the stylet 124. Typically, the stylet 124 has a smaller radius of curvature, or a tighter bend, than the sheath 122. Therefore, as shown in FIG. 8, when the stylet 124 is disposed within the lead 100, extension of the lead 100 and stylet 124 through the sheath 122 bends or directs the lead 100 through a first curvature 123. Further extension of the lead 100 and stylet 124 beyond the distal end 128 of the sheath 122 allows the lead 100 to bend further along a second curvature 125. This allows the lead 100 to make sharp turns and extended curvatures, such as around one or more pedicles.

Figure 9A:
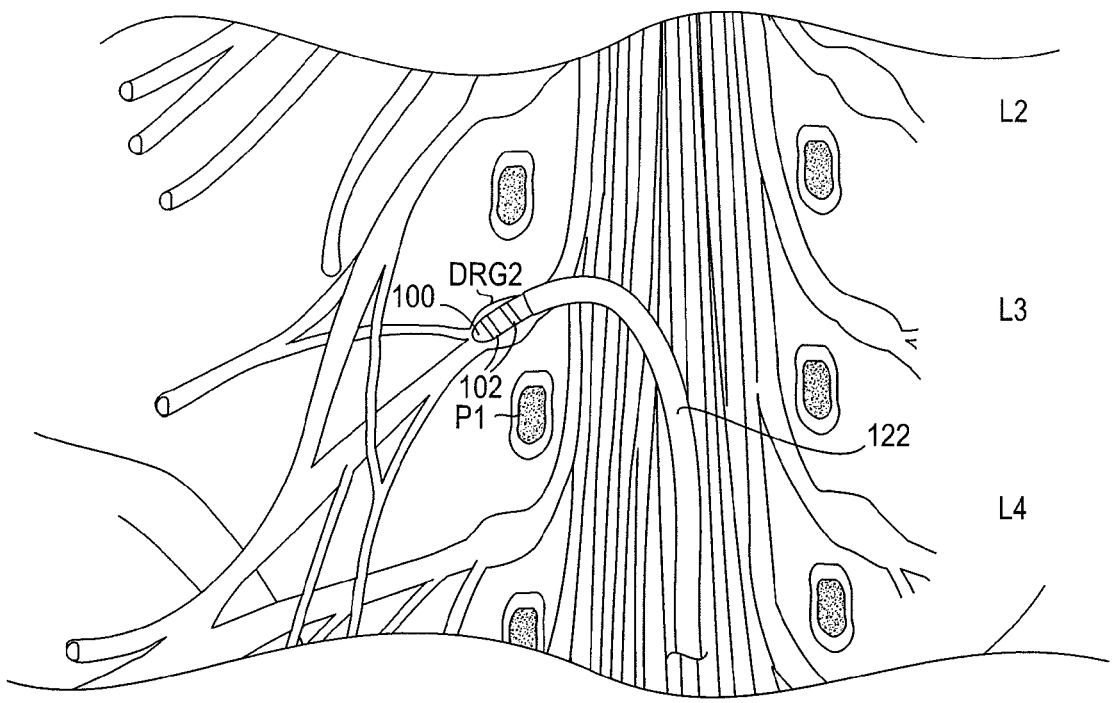
FIGS. 9A-9B illustrate an embodiment of a method of delivering a lead to a position as illustrated as in FIG. 2A.
Figure 9B:
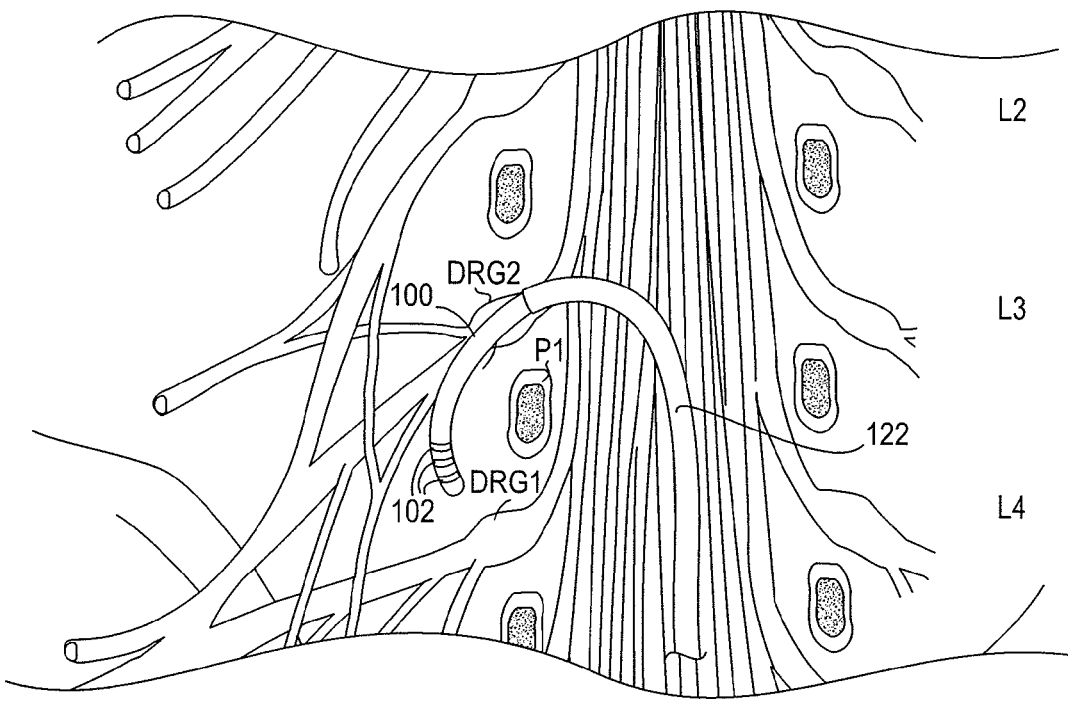

FIGS. 9A-9B illustrate an embodiment of the lead 100 and delivery system 120 of FIGS. 6A-6D used in positioning the lead 100 as in FIG. 2A. Here, the sheath 122 is advanced over the shaft 103 of the lead 100. Passage of the sheath 122 over the lead 100 causes the lead 100 to bend in accordance with the precurvature of the sheath 122. Thus, the sheath 122 assists in steering the lead 100 along the spinal canal S and in a lateral direction toward a target DRG2. FIG. 9A illustrates the sheath 122 positioned so as to direct the lead 100 toward the target DRG2, and the lead 100 is shown advanced beyond the distal end of the sheath 122. FIG. 9B illustrates the lead 100 advanced further beyond the distal end of the sheath 122. Within the lead 100 is the stylet 124 which is pre-curved and causes the lead 100 to bend in accordance with the precurvature of the stylet 124. This bending guides the lead 100 around the pedicle P1 and directs the distal end of the lead 100 toward the target DRG1. The lead 100 may be further advanced to desirably position the first grouping A of electrodes 102 near DRG1 and the second grouping B of electrodes 102 resides near DRG2. The stylet 124 and sheath 122 are then removed and the lead 100 left in place.

Thus, the lead 100 does not require stiff or torqueable construction since the lead 100 is not torqued or steered by itself. The lead 100 is positioned with the use of the sheath 122 and stylet 124 which direct the lead 100 through the two step curvature. This eliminates the need for the operator to torque the lead 100 and optionally the sheath 122 with multiple hands. This also allows the lead 100 to have a lower profile as well as a very soft and flexible construction. This, in turn, minimizes erosion and discomfort created by pressure on nerve tissue, such as the target DRG and/or the nerve root, once the lead 100 is implanted. For example, such a soft and flexible lead 100 will minimize the amount of force translated to the lead 100 by body movement (e.g. flexion, extension, torsion).

Referring back to FIG. 6D, an embodiment of an introducing needle 126 is illustrated. When using an epidural approach, the introducing needle 126 is used to access the epidural space of the spinal cord S. The needle 126 has a hollow shaft 127 and typically has a very slightly curved distal end 132. The shaft 127 is sized to allow passage of the lead 100, sheath 122 and stylet 124 therethrough. In some embodiments, the needle 126 is 14 gauge which is consistent with the size of epidural needles used to place conventional percutaneous leads within the epidural space. However, it may be appreciated that other sized needles may also be used, particularly smaller needles such as 16-18 gauge. Likewise, it may be appreciated that needles having various tips known to practitioners or custom tips designed for specific applications may also be used. The needle 126 also typically includes a Luer-Lok™ fitting 134 or other fitting near its proximal end.

The Luer-Lok™ fitting 134 is a female fitting having a tabbed hub which engages threads in a sleeve on a male fitting, such as a syringe.

Example leads, delivery systems and methods of approaching a target DRG using the delivery system 120 and other delivery systems are further described and illustrated in U.S. Provisional Patent Application No. 61/144,690 filed Jan. 14, 2009, and U.S. Non-Provisional patent application Ser. No. 12/687,737 filed Jan. 14, 2010, both incorporated herein by reference for all purposes. In particular, multiple sheaths may be used to desirably direct the lead 100 into its desired position. For example, an additional sheath may be used with the above described delivery system 120. In such situations, the additional sheath is advanceable through sheath 122, and the lead 100 is advanceable through the additional sheath. The additional sheath may be straight or may have any desired curvature. For example, the additional sheath may be curved to direct a lead 100 around a pedicle. The additional sheath has a stiffness that allows for directing a relatively floppy lead. Alternatively, a stiffer lead may be used to provide directional control.

Figure 10A:
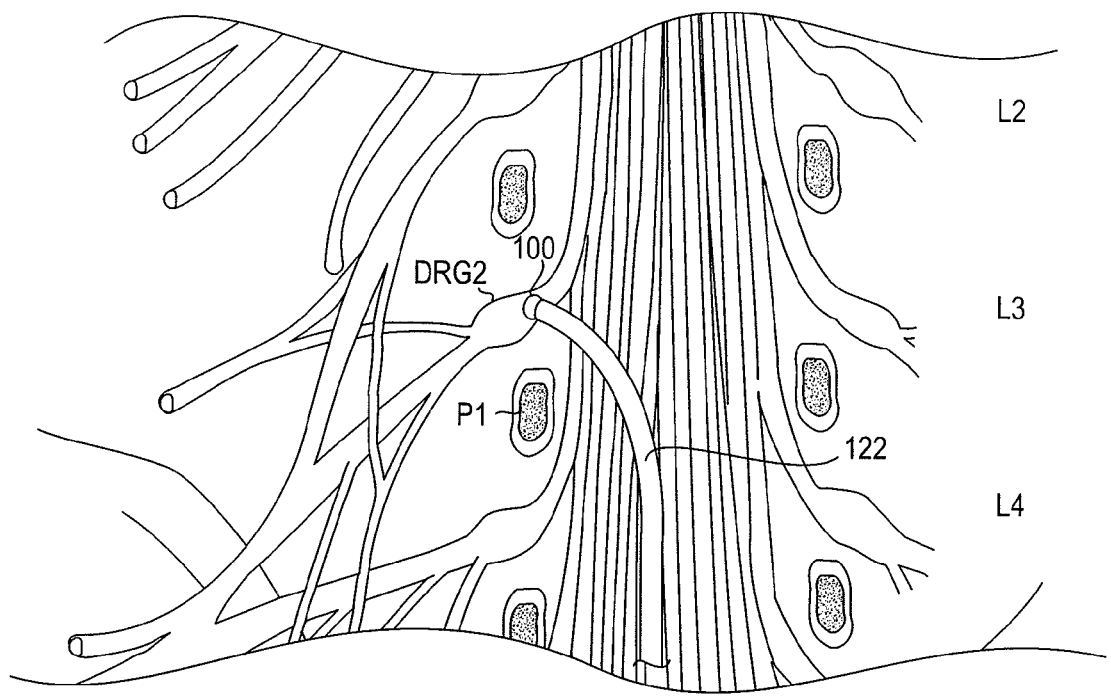
FIGS. 10A-10D illustrate an embodiment of a method of using multiple sheaths to deliver a lead to a position as illustrated in FIG. 2A.
Figure 10B:
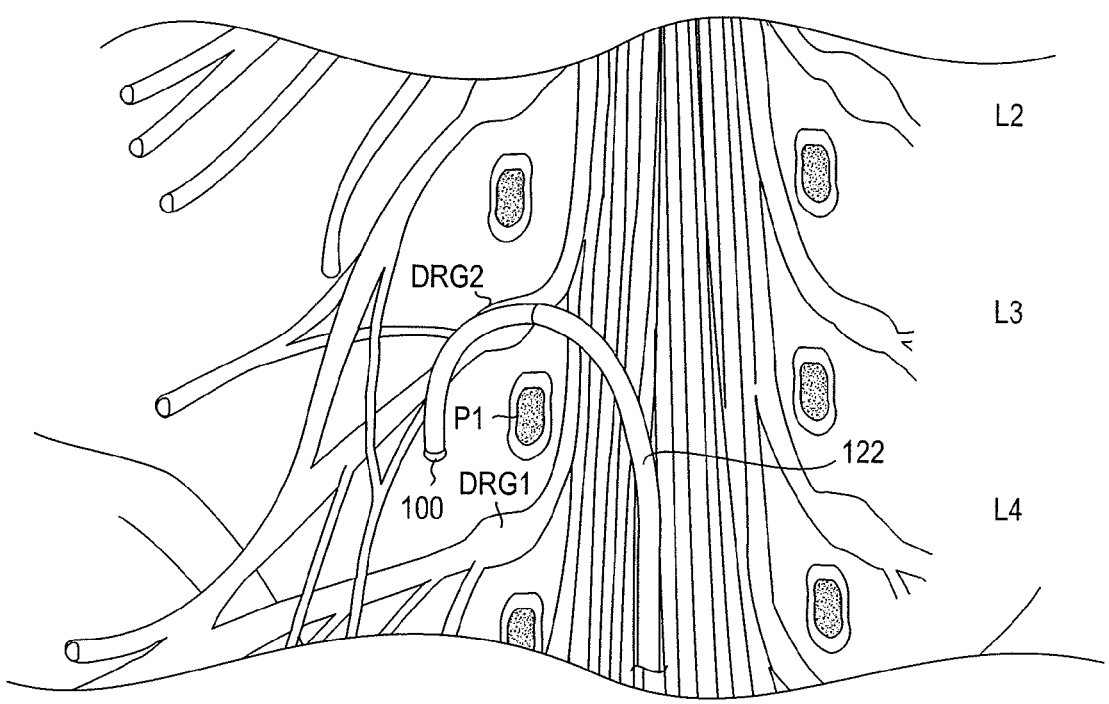
Figure 10C:
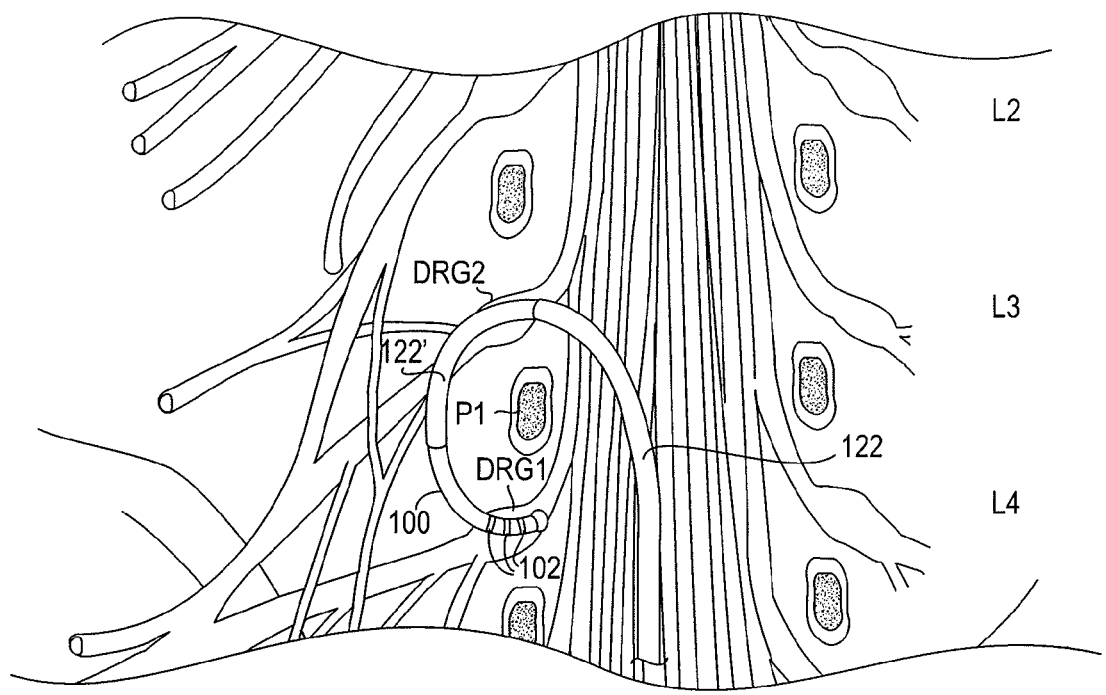
Figure 10D:
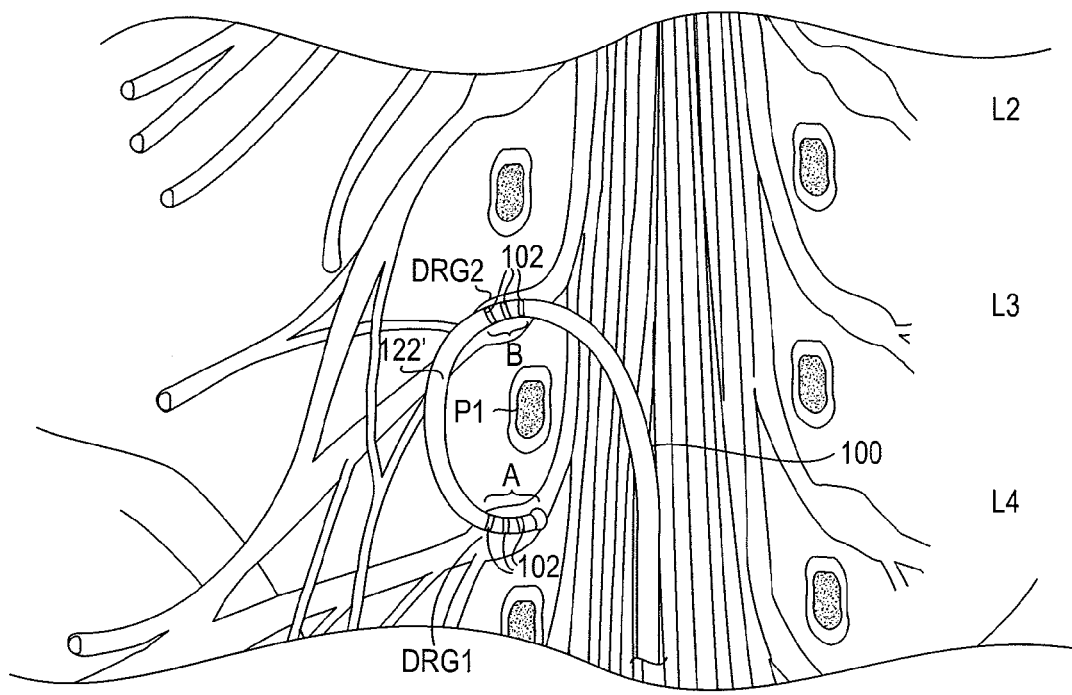

FIGS. 10A-10D illustrate an embodiment of the lead 100 and delivery system 120 of FIGS. 6A-6D, with the addition of an additional sheath 122', used in positioning the lead 100 as in FIG. 2A. Referring to FIG. 10A, the multiple sheaths, sheath 122 and sheath 122' (disposed therein), is advanced over the shaft 103 of the lead 100 and positioned so as to direct the lead 100 toward a target DRG2. As mentioned previously, the pre-curvature of the sheaths causes the lead 100 to bend, as in a lateral direction toward DRG2. FIG. 10B illustrates the additional sheath 122' advanced beyond the distal end of the sheath 122. The pre-curvature of the additional sheath 122' assists in bending the lead around the pedicle P1. FIG. 10C illustrates the lead 100 advanced beyond the distal end of the additional sheath 122'. Within the lead 100 is the stylet 124 which is pre-curved and causes the lead 100 to bend in accordance with the precurvature of the stylet 124. This bending guides the lead 100 further around the pedicle P1 and directs the distal end of the lead 100 toward the target DRG1. The lead 100 may be further advanced to desirably position the first grouping A of electrodes 102 near DRG1 and the second grouping B of electrodes 102 resides near DRG2. The sheaths 122, 122' are then removed and the lead 100 left in place, as illustrated in FIG. 10D. It may be appreciated that various sub-combinations of delivery tools may alternatively be used, such as multiple sheaths without a stylet.

It may also be appreciated that other types of leads and corresponding delivery systems may be used to position such leads in orientations illustrated and described herein. For example, the lead may have a pre-curved shape wherein the lead is deliverable through a sheath having a straighter shape, such as a substantially straight shape or a curved shape which is has a larger radius of curvature than the lead. Advancement of the lead out of the sheath allows the lead to recoil toward its pre-curved shape. Various combinations of curvature between the lead and sheath may allow for a variety of primary and secondary curvatures. Once the lead is desirably placed, the sheath may then be removed.

Figure 11:
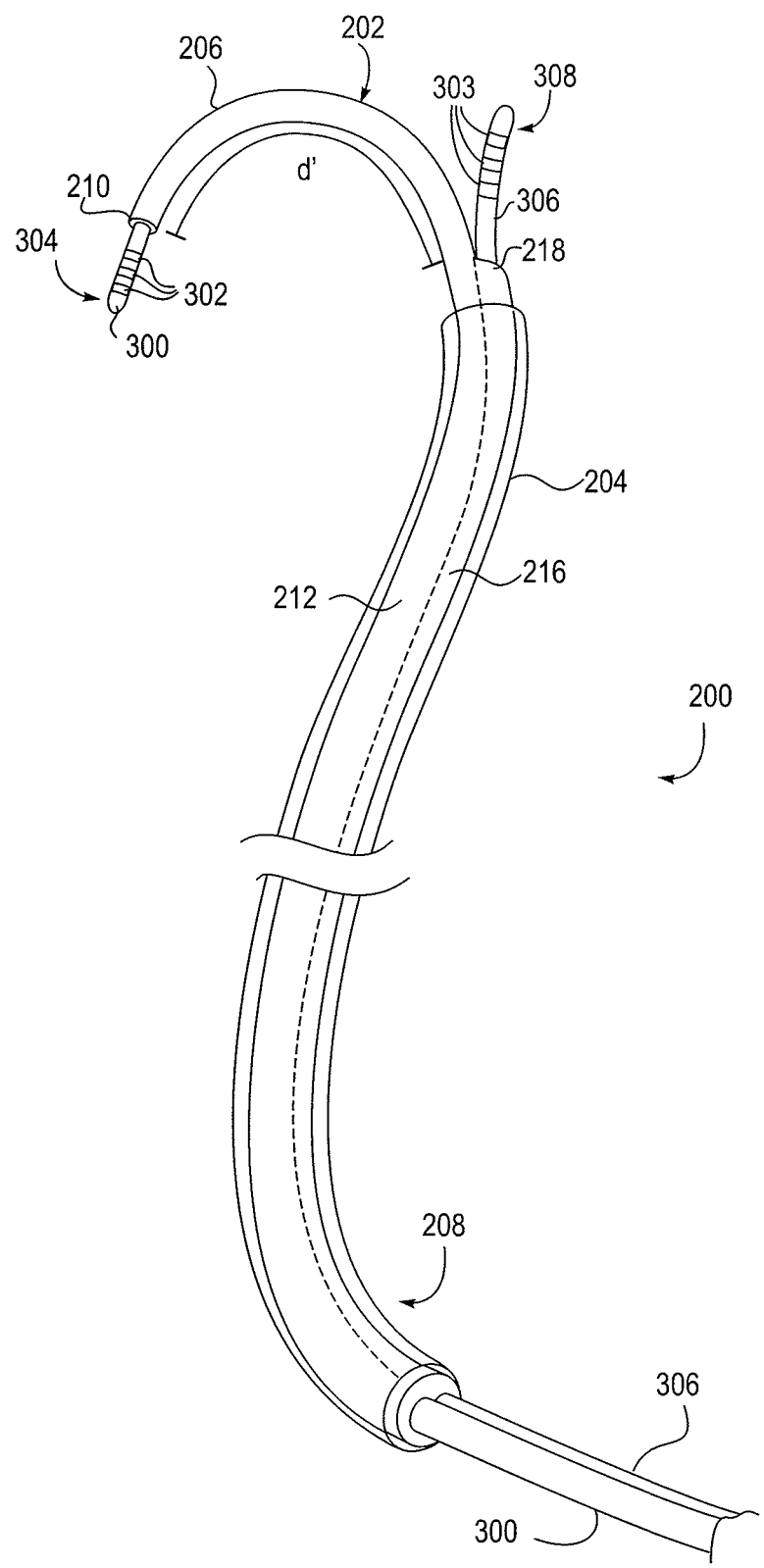
FIG. 11 illustrates an embodiment of a delivery system for delivering two separate leads.

Referring back to FIG. 5A, the single lead 100 is shown stimulating two DRGs, DRG1 and DRG2. In other embodiments, two DRGs are stimulated with a similar extraforaminal approach, however two separate leads are delivered. FIG. 11 illustrates an embodiment of a delivery system 200 used for such a delivery. The delivery system 200 includes a delivery device 202 and an introducer 204. The delivery device 202 comprises a shaft 206 having a proximal end 208 and a distal tip 210. The shaft 206 includes a first lumen 212 extending from the proximal end 208 to or near the distal tip 210. A first lead 300 having at least one electrode 302 disposed near its distal end 304 is advanceable through the first lumen 212, as shown, so that the at least one electrode 302 is advanceable beyond the distal tip 210 of the delivery device 202. The shaft 206 also includes a second lumen 216 extending from the proximal end 208 to a port 218 disposed along the shaft 206. A second lead 306 having at least one electrode 303 disposed near its distal end 308 is advanceable through the second lumen 216, as shown, so that the at least one electrode 303 is advanceable through the port 218. The port 218 is disposed a distance d' from the distal tip 210. The distance d' allows for the first lead 300 to be delivered so that the at least one electrode 302 is positioned near a first target anatomy and allows for the second lead 306 to be delivered so that the at least one electrode 303 is disposed near a second target anatomy. Thus, the distance d' may be equal to the distance d in the above described embodiments.

In some embodiments, the shaft 206 is shaped, such as curved, so as to direct the leads 300, 306 in desired directions, such as opposite directions. The introducer 204 is typically comprised of a material which provides enough rigidity to sufficiently straighten the shaped portion of the shaft 206 upon advancement of the introducer 204 over the shaft 206. In some embodiments, the introducer 204 comprises a needle. In other embodiments, the introducer 204 comprises a sheath.

Figure 12A:
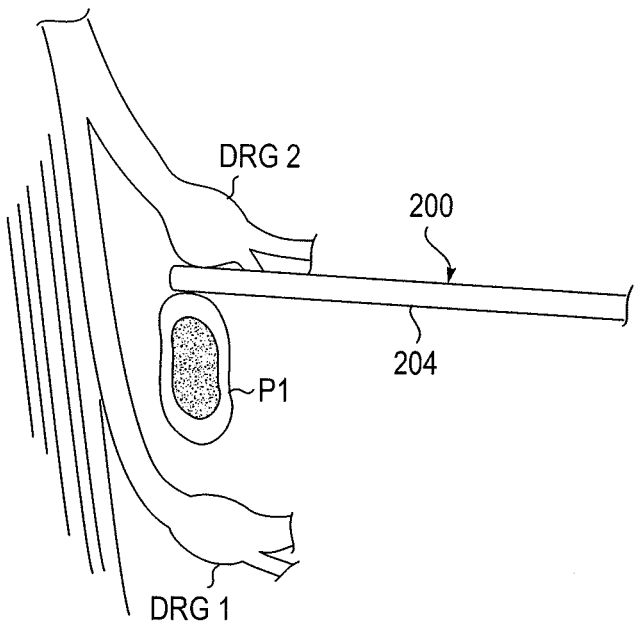
FIGS. 12A-12E illustrate an example method of delivering leads with the use of the delivery system of FIG. 11.
Figure 12B:
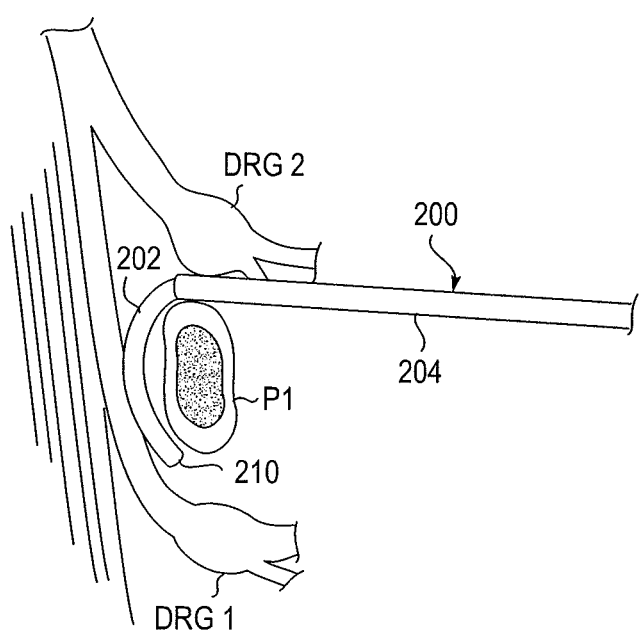
Figure 12C:
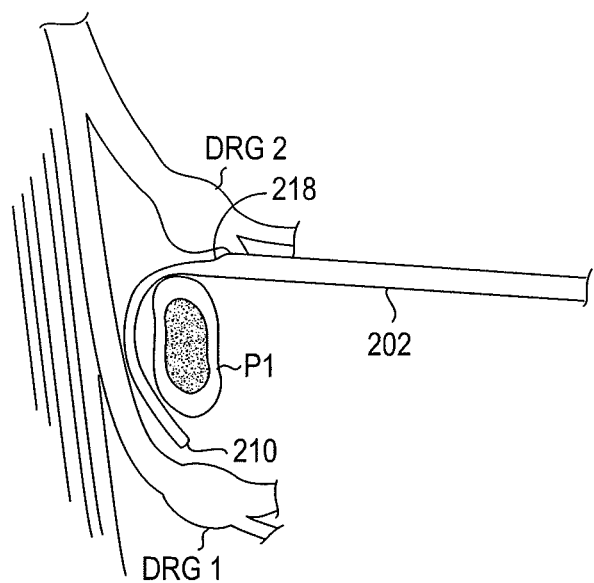
Figure 12D:
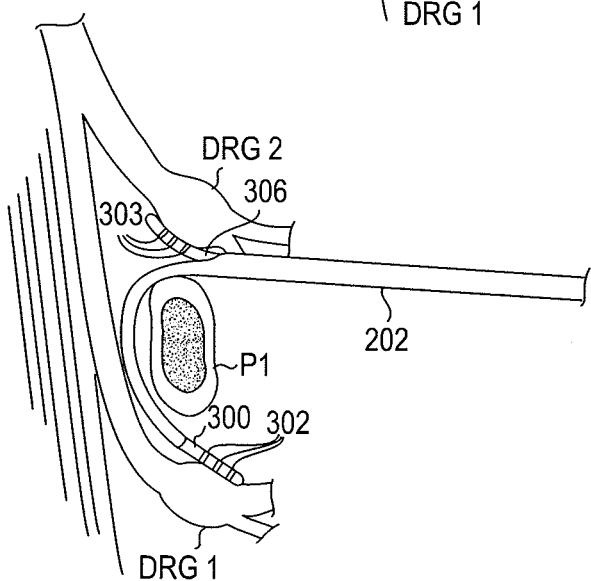
Figure 12E:
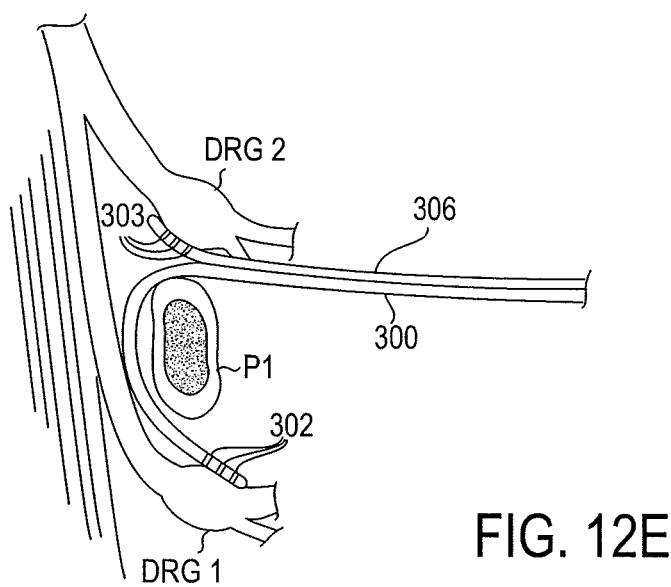

FIGS. 12A-12E illustrate an example method of delivering the leads 300, 306 with the use of the delivery system 200. In this example, the first target anatomy comprises DRG1 on a first level and the second target anatomy comprises DRG2 on a second level, wherein a pedicle P1 resides therebetween. Referring to FIG. 12A, the system 200 is advanced toward DRG2, above the pedicle P1. The system 200 is configured so that the introducer 204 is advanced over the delivery device 202 which causes the device 202 to form a straightened configuration therein. Referring to FIG. 12B, a portion of the device 202 is then advanced beyond the introducer 204. Once released from the introducer 204, the device 202 resumes its curved shape which directs the distal tip 210 of the device 202 around the pedicle P1, toward DRG1. Referring to FIG. 12C, the introducer 204 is then removed and the device 202 is left in place. As shown, the device 202 is positioned so that the distal tip 210 is directed toward the first target anatomy (DRG1) and the port 218 is directed toward the second target anatomy (DRG2). Referring to FIG. 12D, lead 300 is advanced through the first lumen 212 so that one or more of the at least one electrode 302 emerges from the distal tip 210. The lead 300 is further advanced until the at least one electrode 302 is desirably positioned in relation to DRG1. Likewise, lead 306 is advanced through the second lumen 216 so that one or more of the at least one electrode 303 emerges from the port 218. The lead 306 is further advanced until the at least one electrode 303 is desirably positioned in relation to DRG2. Referring to FIG. 12E, the delivery device 202 is then retracted leaving the leads 300, 306 in place.

Figure 13:
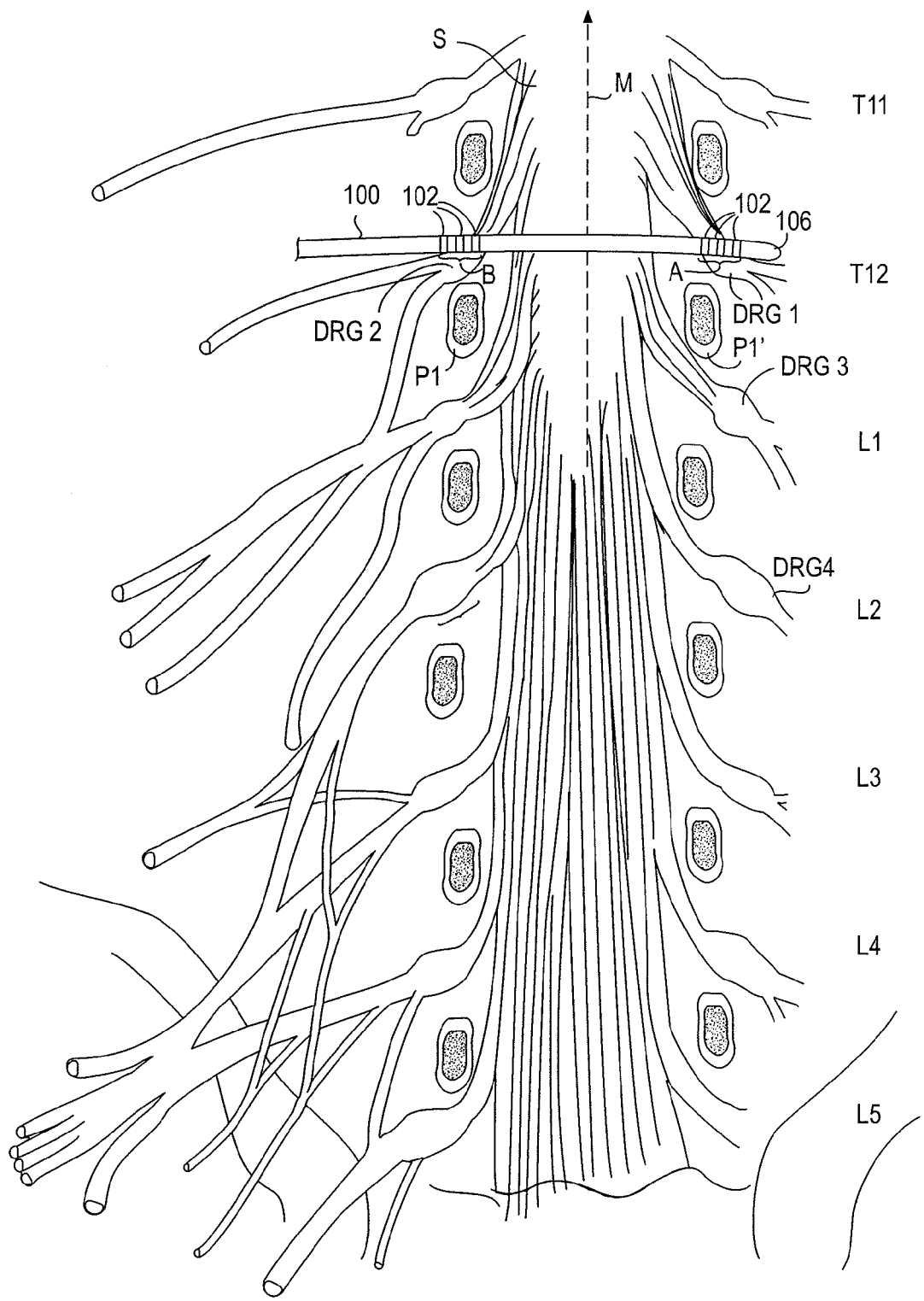
FIG. 13 illustrates another example positioning of the lead of FIG. 1 within a patient anatomy.

FIG. 13 illustrates another example positioning of the lead 100 of FIG. 1 within a patient anatomy wherein the first grouping A of electrodes 102 resides near a first target anatomy and the second grouping B of electrodes 102 resides near a second target anatomy. In this example, the first target anatomy is a DRG1 on a first level (T12) and the second target anatomy is a DRG2 on the same level (T12). Here, the lead 100 is advanced extraforaminally, or from an "outside-in" approach along a peripheral nerve P toward a DRG and a spinal canal S. To begin, the distal tip 106 of the lead 100 is advanced toward DRG2 and through the corresponding intervertebral foramen along the first level (T12). The distal tip 106 is further advanced across the midline M or the spinal canal S toward DRG1 along the same level (T12) (and may pass through the corresponding intervertebral foramen depending on the location of DRG1). In this embodiment, the distal tip 106 is positioned so that the first grouping A of electrodes 102 resides near DRG1 and the second grouping B of electrodes 102 resides near DRG2. In FIG. 13, the lead 100 is illustrated such that the electrode groupings A, B are disposed on the respective DRGs, however it may be appreciated that the groupings A, B may reside at various locations on or in the vicinity of the respective DRGs. Likewise, the lead 100 may be positioned against the pedicles P1, P1' at one or more locations. It may also be appreciated that the lead 100 may be positioned anterior or posterior to the dura mater within the spinal canal S.

In other embodiments, the lead 100 may be similarly positioned to stimulate target anatomies on opposite sides of the spinal column and on differing levels. For example, in some embodiments the first target anatomy is a DRG1 on a first level (T12) and the second target anatomy is a DRG3 on an adjacent level (L1). Or, in other embodiments, the first target anatomy is a DRG1 on a first level (T12) and the second target anatomy is a DRG4 on an non-adjacent level (L2). In each of these embodiments, the lead 100 is steered with the use of a delivery system, such as described above.

Figure 14:
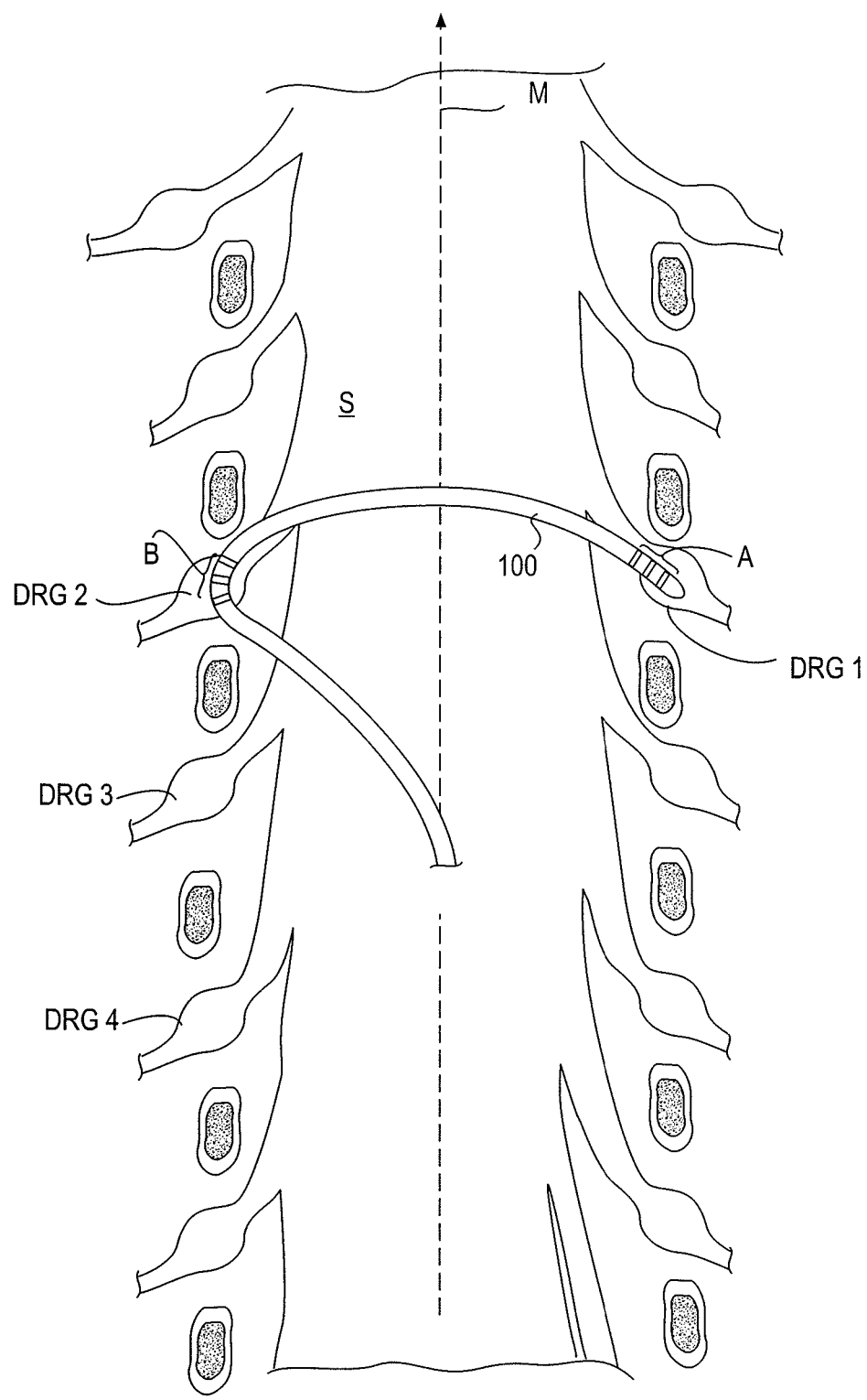
FIG. 14 an example positioning of the lead within the epidural space so as to stimulate target anatomies on opposite sides of the spinal column.

FIG. 14 illustrates another example positioning of the lead 100 so as to stimulate target anatomies on opposite sides of the spinal canal and optionally on differing levels. In this embodiment, the first target anatomy is a DRG1 on a first level and the second target anatomy is a DRG2 on the same level. Here, the lead 100 is advanced epidurally, in an antegrade direction, along the spinal canal S. The distal tip is positioned so that the first grouping A of electrodes 102 resides near DRG1, such as with the use of the delivery system 120 described above. The lead 100 is then extended across the midline M of the spinal canal S on the same spinal level, and the second grouping B of electrodes 102 is positioned near the second target anatomy DRG2. Thus, a single lead is able to stimulate two different target anatomies on the same spinal level. It may be appreciated that the lead 100 may similarly be positioned so as to stimulate target anatomies on different spinal levels. In such embodiments, the lead 100 extends across the midline M of the spinal canal S to a different spinal level, and the second grouping B of electrodes 102 is positioned near a target anatomy such as DRG3 or DRG 4. Likewise, it may be appreciated that the lead may be positioned in a variety of configurations, such zig-zagging across the spinal canal S to stimulate target anatomies on a variety of levels and/or on the same or opposite sides of the spinal canal S, and the electrodes may be disposed at any location along the lead to correspond to such positioning. It may also be appreciated that the lead may be positioned using any suitable approach, including a retrograde, contralateral, ipsilateral or extraforaminal approach, to name a few.

Figure 15A:
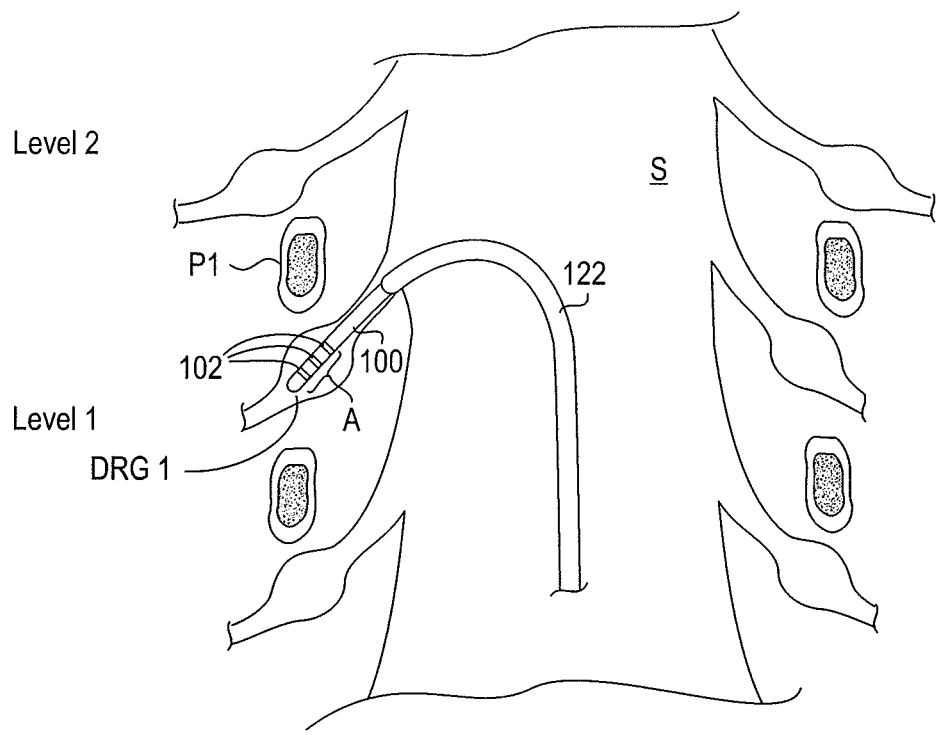
FIGS. 15A-15D illustrate an embodiment of a method of positioning a lead so as to stimulate target anatomies on two different spinal levels without exiting the epidural space or crossing the midline of the spinal canal.
Figure 15B:
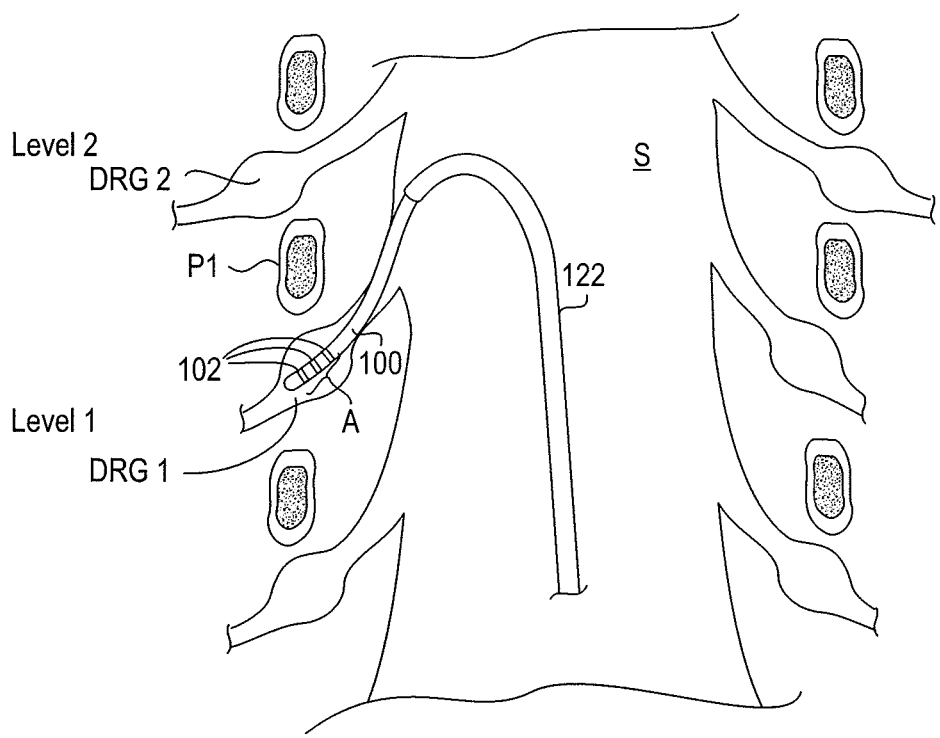
Figure 15C:
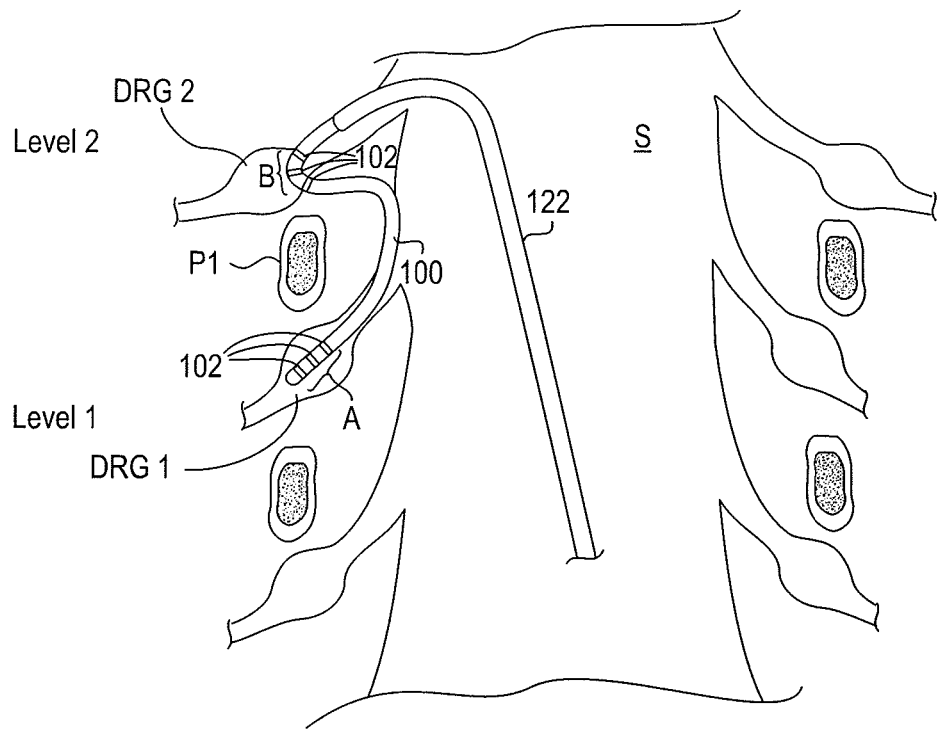
Figure 15D:
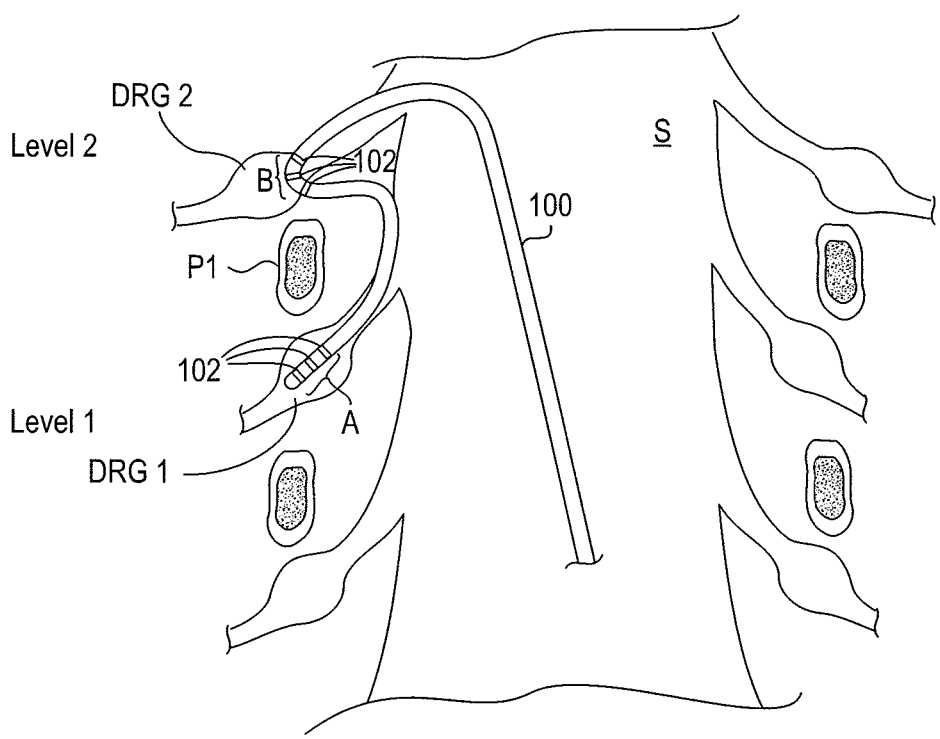

FIGS. 15A-15D illustrates another example positioning of the lead 100 of FIG. 1 within a patient anatomy wherein the first grouping A of electrodes 102 resides near a first target anatomy and the second grouping B of electrodes 102 resides near a second target anatomy. In this example, the first target anatomy is DRG1 on a first level and the second target anatomy is DRG2 on an adjacent, second level. Referring to FIG. 15A, the first grouping A of electrodes 102 is positioned near the first target anatomy DRG1 with the use of the delivery system 120 described above. As shown, the sheath 122 is advanced over the lead 100 and assists in directing the lead 100 laterally outwardly, toward DRG1, along with the assistance of the stylet 124 within the lead 100. The stylet 124 is then retracted and the sheath 122 is advanced along the spinal canal S while the distal end of the lead 100 remains in place, as illustrated in FIG. 15B. As the sheath 122 is advanced, the lead 100 wraps at least partially around an internal border of the pedicle P within the epidural space. Once the sheath 122 has advanced to the adjacent, second level, the sheath 122 is manipulated so as to direct the lead 100 toward the second target anatomy DRG2, as illustrated in FIG. 15C. The stylet 124 may also be advanced to assist in directing the lead 100 toward the second target anatomy DRG2 and desirably positioning the second grouping of electrodes 102 near DRG2. The sheath 122 and stylet 124 are then removed and the lead 100 left in place, as illustrated in FIG. 15D. Thus, a single lead is able to stimulate target anatomies on two different spinal levels without exiting the epidural space or crossing the midline of the spinal canal S. It may be appreciated that although this example illustrates an antegrade approach, the lead may be positioned using any suitable approach, including a retrograde, contralateral, ipsilateral or extraforaminal approach, to name a few.

It may be appreciated that the methods, devices and systems described herein may be used to stimulate a variety of target anatomies throughout the body. For example, in some embodiments the first grouping A of electrodes 102 resides along the spinal cord, such as along the midline of the spinal cord, and the second grouping of electrodes resides near a DRG. In other embodiments, the second grouping of electrodes resides along a dorsal root. In still other embodiments, the second grouping of electrodes resides along a dorsal root entry zone (DREZ). And in still other embodiments, the second grouping of electrodes resides along a different portion of the spinal cord, such as an area off-set from the midline. In these examples, various types and/or locations of spinal tissue are able to be stimulated with a single lead. This may be desired when the patient is not able to obtain adequate pain relief by stimulating one anatomical area wherein stimulation of an additional area is needed. For example, patients having leg radiculopathy and axial back pain may desire dorsal column stimulation to achieve pain relief in the legs and DRG stimulation to achieve pain relief of the back. Such stimulation may be achieved with the use of a single lead utilizing the methods, devices and systems of the present invention.

A variety of pain-related conditions are treatable with the systems, methods and devices of the present invention. In particular, the following conditions may be treated:
1) Failed Back Surgery syndrome
2) Chronic Intractable Low Back Pain due to:
   A) Unknown Etiology
   B) Lumbar facet disease as evidenced by diagnostic block(s)
   C) Sacroiliac Joint disease as evidenced by diagnostic block(s)
   D) Spinal Stenosis
   E) Nerve root impingement—non-surgical candidates
   F) Discogenic Pain—discography based or not
3) Complex Regional Pain Syndrome Wait, renumbering:
4) Complex Regional Pain Syndrome
5) Post-Herpetic Neuralgia
6) Diabetic Neuropathic Pain
7) Intractable Painful Peripheral Vascular Disease
8) Raynaud's Phenomenon
9) Phantom Limb Pain
10) Generalized Deafferentation Pain Conditions
11) Chronic, Intractable Angina
12) Cervicogenic Headache
13) Various Visceral Pains (pancreatitis, etc.)
14) Post-Mastectomy Pain
15) Vulvodynia
16) Orchodynia
17) Painful Autoimmune Disorders
18) Post-Stroke Pain with limited painful distribution
19) Repeated, localized sickle cell crisis
20) Lumbar Radiculopathy
21) Thoracic Radiculopathy
22) Cervical Radiculopathy
23) Cervical axial neck pain, "whiplash"
24) Multiple Sclerosis with limited pain distribution Likewise, the following non-painful indications or conditions are also treatable with the systems, methods and devices of the present invention:
1) Parkinson's Disease
2) Multiple Sclerosis
3) Demylenating Movement Disorders
4) Physical and Occupational Therapy Assisted Neurostimulation
5) Spinal Cord Injury—Neuroregeneration Assisted Therapy
6) Asthma
7) Chronic Heart Failure
8) Obesity
9) Stroke—such as Acute Ischemia Although the foregoing invention has been described in some detail by way of illustration and example, for purposes of clarity of understanding, it will be obvious that various alternatives, modifications, and equivalents may be used and the above description should not be taken as limiting in scope of the invention which is defined by the appended claims.

What is claimed is:

1. A method comprising:
   advancing a lead into a body of a patient through an epidural space of the body, the lead comprising a shaft having a distal tip and at least one electrode disposed a distance along the shaft proximal to the distal tip;
   positioning the distal tip near a first dorsal root ganglion by initially passing out from the epidural space through an intervertebral foramen associated with a second dorsal root ganglion and guiding the distal tip past the second dorsal root ganglion and then inward toward the first dorsal root ganglion, wherein the first and second dorsal root ganglia are on different spinal levels;
   positioning the at least one electrode near the second dorsal root ganglion; and
   stimulating the second dorsal root ganglion with the at least one electrode.

2. A method as in claim 1, wherein positioning the distal tip near the first dorsal root ganglion comprises wrapping at least a portion of the distance along the shaft around at least a portion of a pedicle.

3. A method as in claim 2, wherein positioning the distal tip near the first dorsal root ganglion comprises passing the distal tip at least partially through an intervertebral foramen associated with the first dorsal root ganglion.

4. A method as in claim 1, wherein the different spinal levels are non-adjacent spinal levels.

5. A method as in claim 1, wherein the lead includes an additional at least one electrode near the distal tip and wherein positioning the distal tip comprises positioning the additional at least one electrode near the first dorsal root ganglion.

6. A method as in claim 1, wherein the shaft of the lead comprises a lumen, the method further comprising advancing a stylet through the lumen so as to bend the shaft.

* * * * *